United States Patent
Enomoto et al.

(10) Patent No.: US 9,778,380 B2
(45) Date of Patent: Oct. 3, 2017

(54) ELECTRONIC CASSETTE

(71) Applicant: FUJIFILM Corporation, Tokyo (JP)

(72) Inventors: Jun Enomoto, Ashikgarakami-gun (JP); Haruyasu Nakatsugawa, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 388 days.

(21) Appl. No.: 14/657,585

(22) Filed: Mar. 13, 2015

(65) Prior Publication Data
US 2015/0276944 A1  Oct. 1, 2015

(30) Foreign Application Priority Data

Mar. 28, 2014 (JP) .................................. 2014-069809

(51) Int. Cl.
*G01T 1/24* (2006.01)
*G01T 1/161* (2006.01)
*G01T 1/175* (2006.01)
*A61B 6/00* (2006.01)
*A61B 8/00* (2006.01)

(52) U.S. Cl.
CPC .......... *G01T 1/244* (2013.01); *A61B 6/4233* (2013.01); *A61B 6/4283* (2013.01); *A61B 8/467* (2013.01); *G01T 1/161* (2013.01); *G01T 1/175* (2013.01)

(58) Field of Classification Search
CPC ..... A61B 6/4405; A61B 6/4233; A61B 6/547; A61B 6/587; A61B 6/461; A61B 6/4429; A61B 6/0492
See application file for complete search history.

(56) References Cited

U.S. PATENT DOCUMENTS

| | | | | |
|---|---|---|---|---|
| 2006/0113481 A1* | 6/2006 | Murphy | ................... | A61B 6/00 250/370.09 |
| 2010/0123083 A1* | 5/2010 | Petrick | ................. | A61B 6/4233 250/370.09 |
| 2011/0075817 A1* | 3/2011 | Takahashi | .............. | G03B 42/04 378/189 |
| 2016/0174918 A1* | 6/2016 | Wang | ................... | A61B 6/4405 378/63 |

FOREIGN PATENT DOCUMENTS

JP  2012-88312 A  5/2012

* cited by examiner

*Primary Examiner* — Hoon Song
(74) *Attorney, Agent, or Firm* — Birch, Stewart, Kolasch & Birch, LLP

(57) ABSTRACT

An electronic cassette is provided with a sensor panel, a housing, operation buttons, a head-bottom setting section, lamps and a memory. The sensor panel has a quadrangle imaging area, and detects an X-ray image of a patient. The housing houses the sensor panel. The operation buttons are disposed on the housing. When either one of the operation buttons is pushed down, the head-bottom setting section sets either one of adjoining two sides of the imaging area to be the head of the radiographic image in the display orientation. The display section is disposed on the housing, and displays which side is set by the head-bottom setting section to be the head of the radiographic image. The memory stores head-bottom setting information and the radiographic image in association with each other.

17 Claims, 28 Drawing Sheets

| OPERATION BUTTON ON/OFF | LAMP ON/OFF | | HEAD-BOTTOM SETTING INFORMATION |
|---|---|---|---|
| OFF | 1ST LAMP | ON | 1ST SHORT SIDE 60A IS HEAD |
| | 2ND LAMP | OFF | |
| ON | 1ST LAMP | OFF | 1ST LONG SIDE 60C IS HEAD |
| | 2ND LAMP | ON | |

| OPERATION BUTTON ON/OFF | LAMP ON/OFF | | HEAD-BOTTOM SETTING INFORMATION |
|---|---|---|---|
| OFF | LAMP | OFF | 1ST SHORT SIDE 60A IS HEAD |
| ON | LAMP | ON | 1ST LONG SIDE 60C IS HEAD |

FIG.24

| | OPERATION BUTTON ON/OFF | | LAMP ON/OFF | | HEAD-BOTTOM SETTING INFORMATION |
|---|---|---|---|---|---|
| 1 | 1ST OPERATION BUTTON | OFF | 1ST LAMP | OFF | 1ST SHORT SIDE 60A IS HEAD |
| | 2ND OPERATION BUTTON | OFF | 2ND LAMP | OFF | |
| 2 | 1ST OPERATION BUTTON | ON | 1ST LAMP | ON | 1ST LONG SIDE 60C IS HEAD |
| | 2ND OPERATION BUTTON | OFF | 2ND LAMP | OFF | |
| 3 | 1ST OPERATION BUTTON | OFF | 1ST LAMP | OFF | 2ND SHORT SIDE 60B IS HEAD |
| | 2ND OPERATION BUTTON | ON | 2ND LAMP | ON | |
| 4 | 1ST OPERATION BUTTON | ON | 1ST LAMP | ON | 2ND LONG SIDE 60D IS HEAD |
| | 2ND OPERATION BUTTON | ON | 2ND LAMP | ON | |

FIG.33

| HEAD-BOTTOM SETTING INFORMATION | IMAGE PROCESSING |
|---|---|
| 1ST SHORT SIDE 60A IS HEAD | STANDARD |
| 1ST LONG SIDE 60C IS HEAD | CONTRAST CORRECTION |

103

ELECTRONIC CASSETTE

CROSS-REFERENCE TO RELATED APPLICATIONS

The present application claims priority under 35 U.S.C. §119 to Japanese Patent Application No. 2014-069809, filed on Mar. 28, 2014. Each of the above application(s) is hereby expressly incorporated by reference, in its entirety, into the present application.

BACKGROUND OF THE INVENTION

1. Field of the Invention

The present invention relates to an electronic cassette and an electronic cassette apparatus for receiving radiation passed through a subject and detecting a radiation image.

2. Description Related to the Prior Art

An electronic cassette is known as a portable X-ray image detector for detecting an X-ray image which represents graphical information on a subject on the basis of radioactive rays, e.g. X-rays, that have penetrated the subject (refer to Japanese Patent Laid-open Publication No. 2012-088312, for example). The electronic cassette consists of a flat portable housing and a sensor panel, also called a flat panel detector (FPD), which is contained in the housing and is capable of outputting data of an X-ray image as digital dat. The sensor panel is provided with a rectangular imaging area which has, for example, a short side and a long side.

The electronic cassette can be used, for example, for round-visit radiography that is performed in a medical ward to take images from a patient who cannot come to an imaging room. In this case, the electronic cassette is carried into the medical ward along with a round-visit vehicle that is an automobile wagon having an X-ray generator boarded thereon. When making a round-visit radiography, a console equipped with an image display is also carried about in addition to the round-visit vehicle and the electronic cassette. The electronic cassette has a function to transmit X-ray images so that X-ray images can be checked on the carried console in the medical ward or the like by transmitting data of the X-ray images to the console immediately after the radiography. Furthermore, the X-ray images may be displayed on an image viewer terminal so that a doctor who has ordered the radiography can serve the X-ray images for diagnosis.

On the image display device of the console or that of the image viewer terminal, the display orientation of each X-ray image is determined with reference to an origin point of the read X-ray image in accordance with the initial default setup. The origin point of the X-ray image coincides with an origin point of an imaging area on the sensor panel of the electronic cassette. The electronic cassette may be used for imagining, for example, in a vertically-long position where the short sides of the rectangular imaging area become the head and bottom of the image, or in a horizontally-long position where the long sides of the imaging area become the head and bottom of the image. On the round-visit radiography, the vertically-long position and the horizontally-long position are selectively used depending upon the situation for imaging such as limited space in the medical ward.

Thus, the imaging position of the electronic cassette varies depending upon the situation. As a result, there may be cases where the subject of the X-ray image is oriented sideways on the image display device when displayed in accordance with the initial setting. In these cases, the radiologist or doctor should change the display orientation of the X-ray image on the image display device by turning the X-ray image through a necessary angle to adjust the subject to the proper orientation.

In order to adjust the image display orientation automatically, Japanese Patent Laid-open Publication No. 2012-088312 discloses an electronic cassette, of which the housing having a rectangular top planar shape is provided with a couple of cable connectors disposed respectively on a short side surface and a long side surface of the housing, these side surfaces being orthogonal to each other. Depending upon which of these cable connectors is connected to cables that transmit X-ray images or supply power to the electronic cassette, the head and bottom of the X-ray image are determined to be short sides or long sides. In the electronic cassette described in the above patent document, for instance, when the cable is connected to the cable connector on the short side, the short side having the cable connector is determined to correspond to the bottom margin of the X-ray image, whereas when the cable is connected to the cable connector on the long side, the long side having the cable connector is determined to correspond to the bottom margin of the X-ray image. Information on the head and bottom of the X-ray image is transmitted to the image display device along with the X-ray image. The image display device determines the head and bottom of the X-ray image on the basis of the received information on the head and bottom, to determine the image display orientation.

However, in some medical fields, like in the round-visit radiography where the electronic cassette should be taken out of the imaging room, there is a need for operating the electronic cassette without carrying a console in order to reduce the number of devices to be carried about. Because the round-visit vehicle is used in the medical ward, cables for the electronic cassette can bother the operation, and therefore wireless communication is desirable in many cases. Meanwhile, the medical ward may be under such circumstances that do not permit wireless communication because there are medical devices that can be affected by electromagnetic waves or wireless communication facilities are not established. In these fields where the use of cables is undesirable, but the wireless communication is not available, the operation without carrying the console is desirable.

The method disclosed in the above patent document, determining the head and bottom of the X-ray image by the choice between the cable connectors, is not applicable to the operation without the cable. However, the cable wiring is actually bothersome and greatly limits the positioning flexibility of the electronic cassette. Furthermore, there may be cases where the cable wiring direction is limited by the positioning condition of the electronic cassette and the spatial condition of the imaging location so that the cable cannot be connected to the desired cable connector to select for the desired display orientation, or even worse, the cable cannot be connected to the electronic cassette. In those cases, it is impossible to select or change the head and bottom of the X-ray image.

SUMMARY OF THE INVENTION

An object of the present invention is to provide an electronic cassette which allows setting the head and bottom in the display orientation of the radiographic image without using the need for any cable or console.

In order to achieve the above object of the present invention, an electronic cassette in accordance with the present invention comprises a sensor panel, a housing, an operating section, a head-bottom setting section, a display section and a memory. The sensor panel has a quadrangle imaging area, and detects a radiographic image of a subject. The housing houses the sensor panel. The operating section is disposed on the housing. The head-bottom setting section sets either one of at least adjoining two sides among four sides of the imaging area to be the head or the bottom of the radiographic image in the display orientation on the basis of an operation command from the operating section. The display section is disposed on the housing, and displays which side is set by the head-bottom setting section to be the head or the bottom of the radiographic image. The memory stores head-bottom setting information from the head-bottom setting section and the radiographic image in association with each other.

The memory preferably stores a plurality of radiographic images in association with individual head-bottom setting information.

It is preferable that the head-bottom setting section is capable of setting any one of the four sides of the imaging area to be the head or the bottom of the radiographic image. Moreover, the quadrangle imaging area is preferably an oblong rectangular imaging area, wherein the adjoining two sides are a short side and a long side.

The electronic cassette is preferably provided with a wireless communicator section for wirelessly transmitting the radiographic image stored in the memory, and a battery for supplying power to the sensor panel. Furthermore, the electronic cassette is preferably provided with a cable connector that is disposed on the housing, for connecting a cable for wired transmission of the radiographic image or power supply from an external power source.

It is preferable that the operating section can work with at least one of pushdown operation, sliding operation and turning operation. It is also preferable that the housing has a transparent panel which lets radioactive rays pass therethrough and a frame member for mounting the transparent panel therein, wherein at least one of the display section and the operating section is provided in the frame member.

Preferably, the operating section is provided on at least one of four side surfaces of the housing, which correspond to the four sides of the imaging area. More preferably, the operating section is provided on at least two side surfaces of the housing, which correspond to the adjoining two sides of the imaging area.

Preferably, the display section is provided on at least one of four side surfaces of the housing, which correspond to the four sides of the imaging area. More preferably, the display section is provided on at least two side surfaces of the housing, which correspond to the adjoining two sides of the imaging area.

The display section is preferably provided at or across a corner at which adjoining two side surfaces of the housing meet. It is also preferable that the housing has four corners at each of which adjoining two side surfaces meet, and the display section is provided at or across each of three corners among the four corners. Furthermore, a corner pad is preferably provided at each corner of the housing, wherein the display section is disposed on either side of the corner pad or behind the corner pad.

The present invention provides an electronic cassette that allows setting the head and bottom in the display orientation of a radiographic image taken by the electronic cassette without the use of any cable or console.

BRIEF DESCRIPTION OF THE DRAWINGS

The above and other objects will be more apparent from the detailed description of the preferred embodiments when read in conjunction with the accompanying drawings wherein like reference numerals designate like or corresponding parts throughout the several views, and wherein:

FIG. 24 is an explanatory diagram illustrating the head-bottom setting data in the electronic cassette of FIG. 23;

FIG. 33 is an explanatory diagram illustrating the correspondence between the head-bottom setting and the image processing of X-ray images.

DESCRIPTION OF THE PREFERRED EMBODIMENTS

First Embodiment

Figure 1:
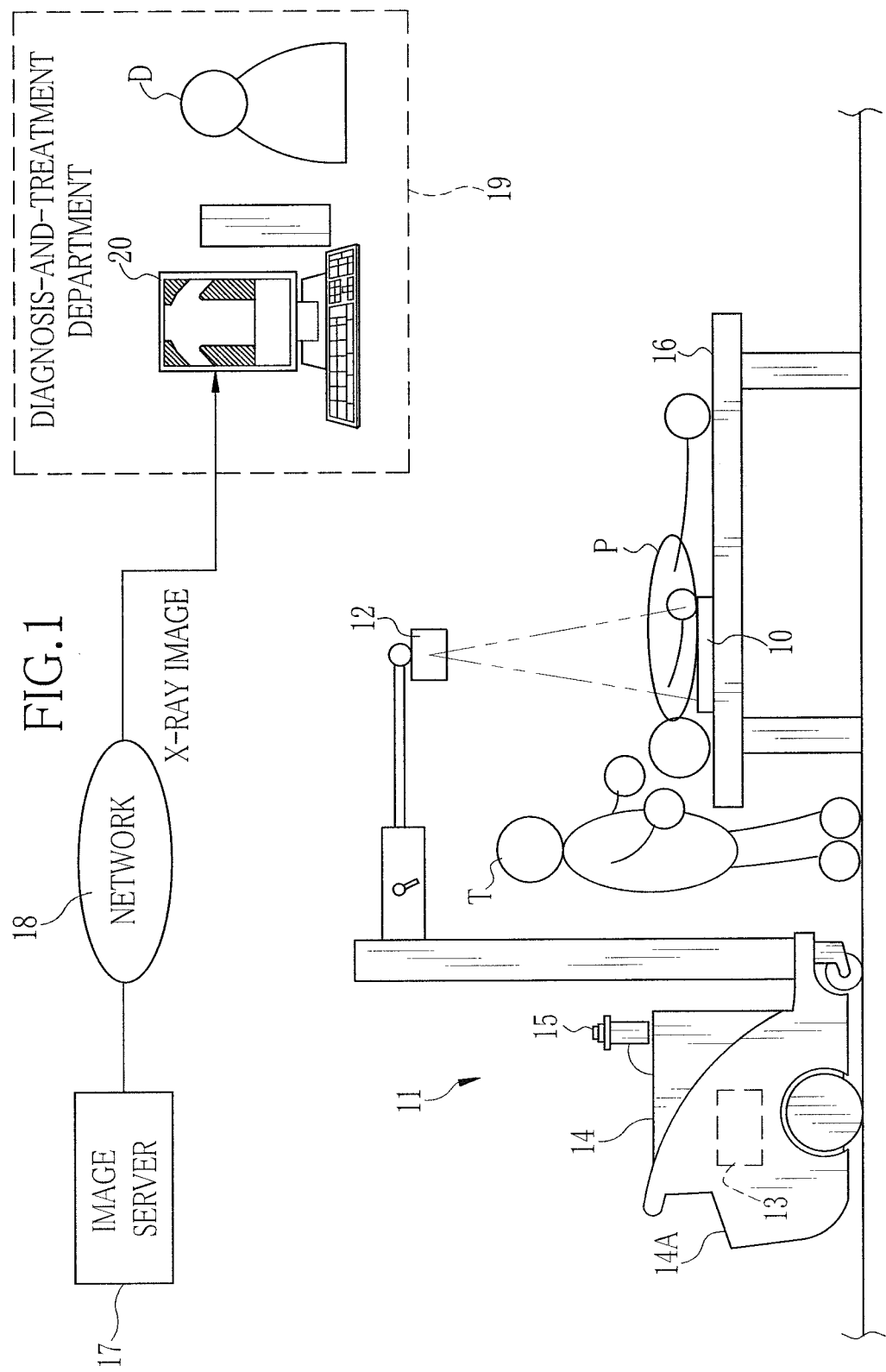
FIG. 1 is a schematic diagram illustrating a structure of an X-ray imaging system using an electronic cassette.

In FIG. 1, an electronic cassette 10 constitutes an X-ray imaging system in combination with a round-visit vehicle 11. The round-visit vehicle 11 is a mobile X-ray generator that has an X-ray source 12 and a source controller unit 13 for controlling the X-ray source 12 boarded on a movable wagon 14. The round-visit vehicle 11 is used for round-visit radiography, moved around a medical ward to take images from those patients P (imaging subjects) who cannot go to the imaging room.

The X-ray source 12 has an X-ray tube for radiating X-rays and a collimator for limiting the irradiation field of X-rays from the X-ray tube. The source controller unit 13 controls the X-ray source 12 on the basis of irradiation conditions including a tube voltage that determines energy spectra of the X-rays, a tube current that determines the amount of radiation per unit time, and an irradiation time for continuing the X-ray irradiation. An activator switch 15 is connected to the source controller unit 13. The activator switch 15 is operated by a radiologist T, to generate a radiation start signal to cause the X-ray source 12 to start an irradiation. The radiation start signal is input to the source controller unit 13 through a signal cable. The movable wagon 14 is provided with a container box 14A for containing the electronic cassettes 10.

When imaging the chest of the patient P, the electronic cassette 10 is inserted in between a bed 16 and the patient P lying on the bed at a position corresponding to the chest of the patient P. The radiating direction from the X-ray source 12 is adjusted to face the electronic cassette 10. The electronic cassette 10 detects an X-ray image of the patient P on the basis of X-rays that have been radiated from the X-ray source 12 and penetrated the patient P.

The electronic cassette 10 has a memory 46 (refer to FIG. 5) for storing X-ray images captured by the electronic cassette 10. At the end of the round-visit radiography, the captured X-ray images are uploaded from the electronic cassette 10 to an image server 17. The image server 17 is connected to a network 18, like a local area network (LAN), such that the image server 17 is accessible from a terminal 20 installed in a diagnosis-and-treatment department 19, a client ordering the radiography, so that the X-ray images can be read from the image server 17 and displayed on the terminal 20. Thus, doctors D can observe the X-ray images.

Figure 2:
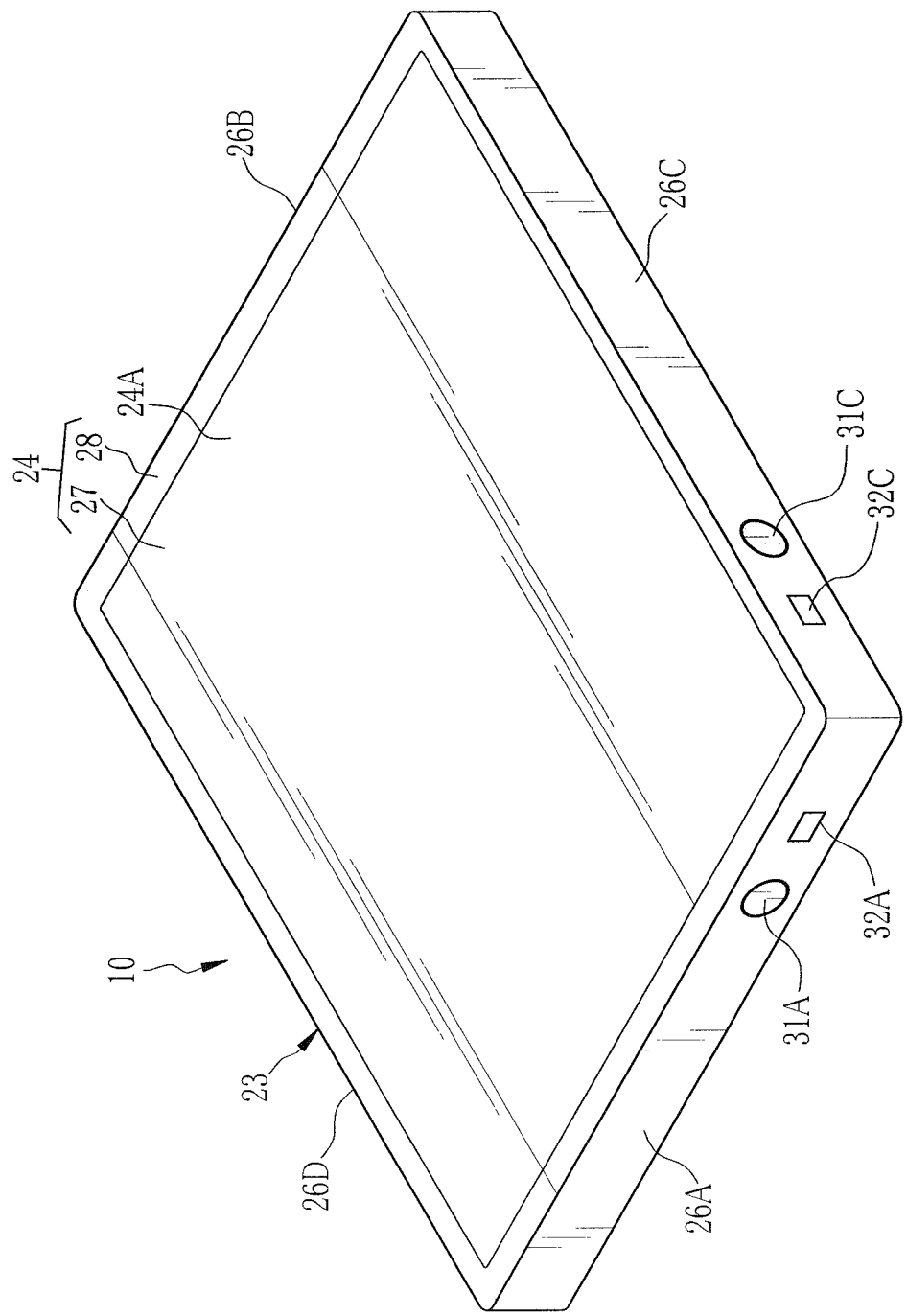
FIG. 2 is a diagrammatic perspective view of an external appearance of an electronic cassette of a first embodiment.
Figure 3:
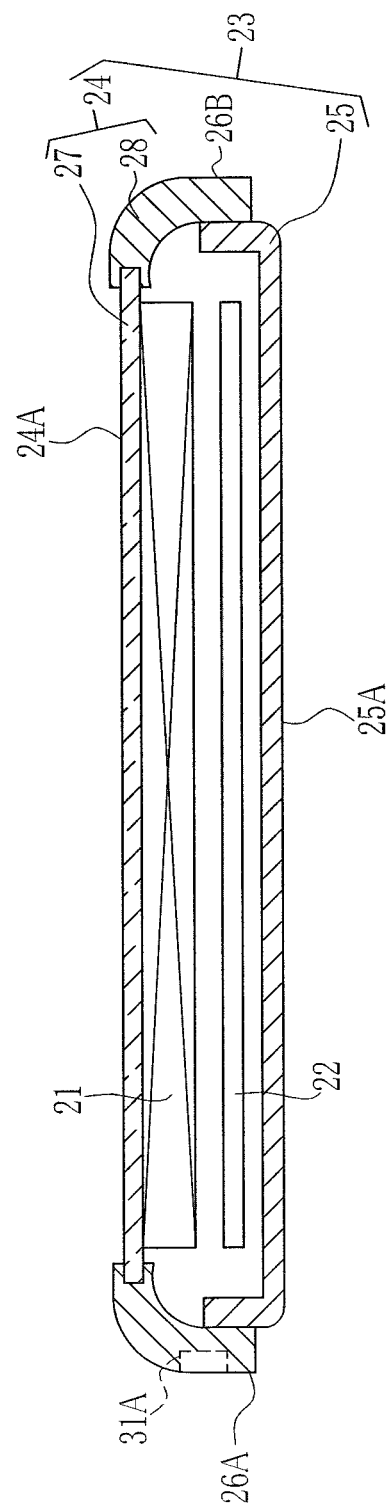
FIG. 3 is a schematic sectional view of the electronic cassette of FIG. 2.

As shown in FIGS. 2 and 3, the electronic cassette 10 has a sensor panel 21, a control circuit board 22 for controlling the sensor panel 21 and a portable housing 23 containing the sensor panel 21 and the control circuit board 22. The sensor panel 21 has an imaging area 30 (refer to FIGS. 4 and 5) of an oblong rectangular shape having short sides and long sides, to capture an X-ray image of an oblong rectangular shape. The housing 23 has a flat cuboid shape having a rectangular top plane, and consists of a front housing 24 and a rear housing 25. The front housing 24 has a front surface 24A that constitutes an incident plane of the X-rays, and the rear housing 25 has a rear surface 25A opposing the front surface 24A. The housing 23 has four side surfaces 26A, 26B, 26C and 26D corresponding to four sides of the imaging area 30. The side surfaces 26A and 26B correspond to opposing two short sides of the imaging area 30, whereas the side surfaces 26C and 26D correspond to opposing two long sides of the imaging area 30.

The front housing 24 consists of a transparent panel 27 that is X-ray permeable, and a frame body 28 having an opening in which the transparent panel 27 is fitted. The transparent panel 27 has an oblong rectangular shape that is approximately equal in size to the imaging area 30. The opening of the frame body 28 also has an oblong rectangular shape, and portions around the opening constitute margins of the front surface 24A and the side surfaces 26A, 26B, 26C and 26D of the housing 23. Note that the cuboid shape of the housing 23 is meant to include approximately cuboid shapes such as one with rounded corners, like the present example, or one with beveled edges. For example, the frame 28 is made of conductive plastics and the transparent panel 27 is made of a carbon graphite. The rear housing 25 is made of a metal such as stainless steel.

The housing 23 has, for example, a plane size in accordance with ISO 4090:2001 standard, like a half-adder-plate size radiographic film cassette (383.5×459.5 mm) or IP (imaging plate) cassettes. Therefore, the electronic cassette 10 may be mounted to a radiographic stand or table which is adapted to the film cassettes and IP cassettes, for use in imaging.

The electronic cassette 10 has a head-bottom setting function for setting the head or bottom position with respect to the display orientation of the X-ray image being captured. As operating members for inputting operation commands for the head-bottom setting, first and second operation buttons 31A and 31C are disposed respectively on two side surfaces 26A and 26C of the housing 23, which correspond to a couple of adjoining short and long sides of the imaging area 30. The first and second operation buttons 31A and 31C are, for example, pushbuttons that can be turned on by pushing it down. Upon one of the operation buttons 31A and 31C being turned on, the other is automatically turned off. Thus, the first operation button 31A and the second operation button 31C are alternatively turned on and off.

First and second lamps 32A and 32C are provided beside the first and second 31A and 31C, respectively. The first and second lamps 32A and 32C are display members for displaying the head position or the bottom position that is set up on the basis of the operation command input through the first operation button 31A or the second operation button 31C. The first lamp 32A and 32C are, for example, light emitting diodes (LEDs).

Figure 4:
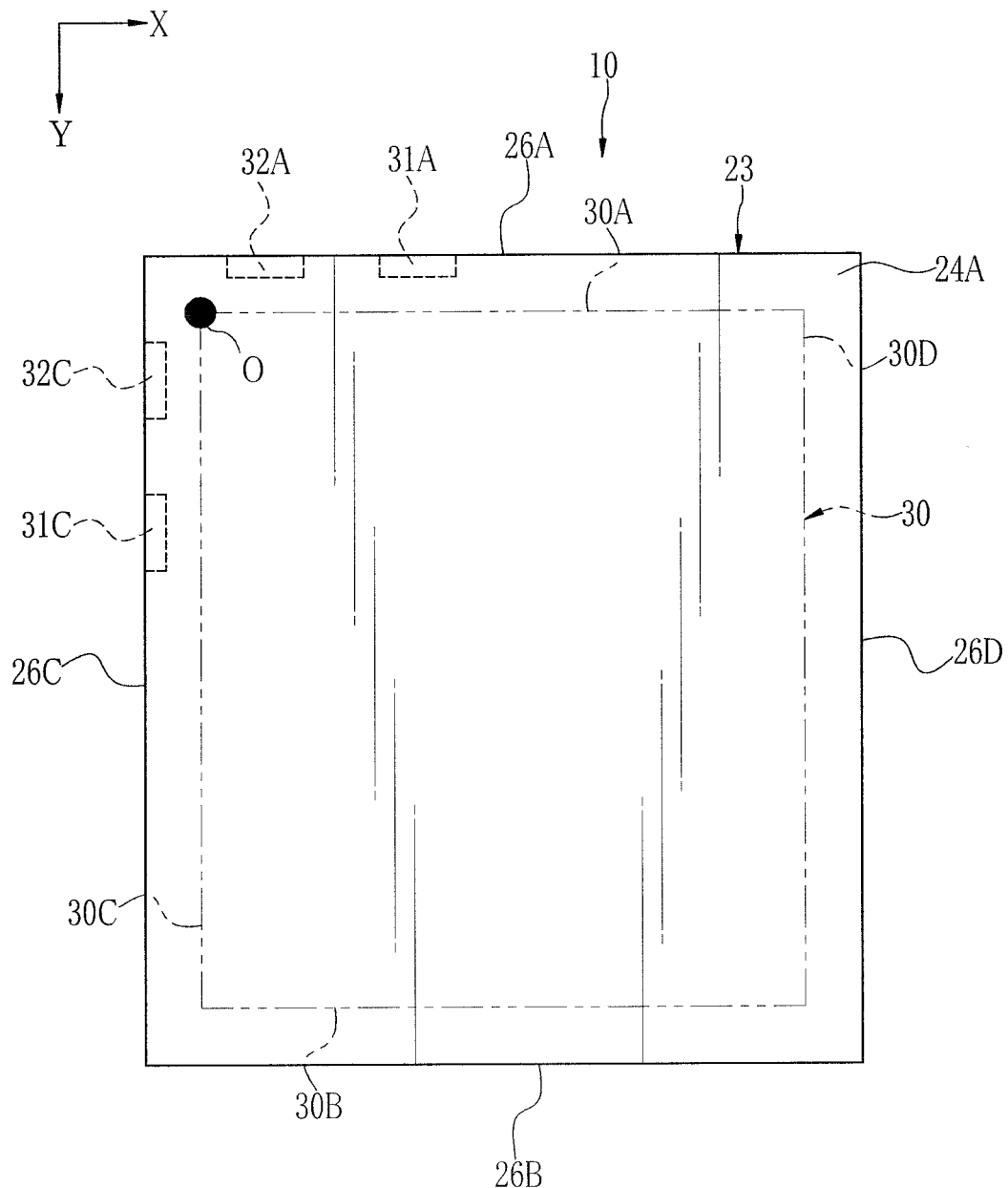
FIG. 4 is a schematic plan view of the electronic cassette of FIG. 2.

As shown in FIG. 4, the imaging area 30 has an oblong rectangular shape having a first short side 30A, a second short side 30B, a first long side 30C and a second long side 30B. In the imaging area 30, an origin O is located at an upper-left corner when viewed in the direction from the front surface 24A of the housing 23, that is, specifically at a vertex between the first short side 30A and the first long side 30C. For example, according to the initial setting of the display orientation of the X-ray image being captured, the first short side 30A is set to be the head of the image and the second short side 30B is the bottom.

When the second operation button 31C is pushed down in this condition, the head-bottom setting in the display orientation is changed such that the first long side 30C is set to be the head of the image and the second long side 30D is the bottom. Thus, with the function for setting the head and bottom in the display orientation, the electronic cassette 10 is switchable between two display orientations: a vertically-long orientation where the first short side 30A and the second short side 30B are set to be the head and bottom and a horizontally-long orientation where the first long side 30C and the second long side 30D are set to be the head and bottom. In the horizontally-long orientation, the displayed image is turned clockwise by 90 degrees from the vertically-long orientation.

In the vertically-long orientation that is initially setup, the first lamp 32A disposed on the side surface 26A is on, as the side surface 26A corresponds to the first short side 30A that is set to be the head in this orientation, whereas the second lamp 32C is off. In the horizontally-long orientation, the second lamp 32C disposed on the side surface 26C is on, as the side surface 26C corresponds to the first long side 30C that is set to be the head in this orientation, whereas the first lamp 32A is off. Thus, either of the first lamp 32A and the second lamp 32C, which corresponds to the side that is set to be the head side, is selectively turned on, enabling to see which side is set to be the head side, the first short side 30A or the first long side 30C.

Figure 5:
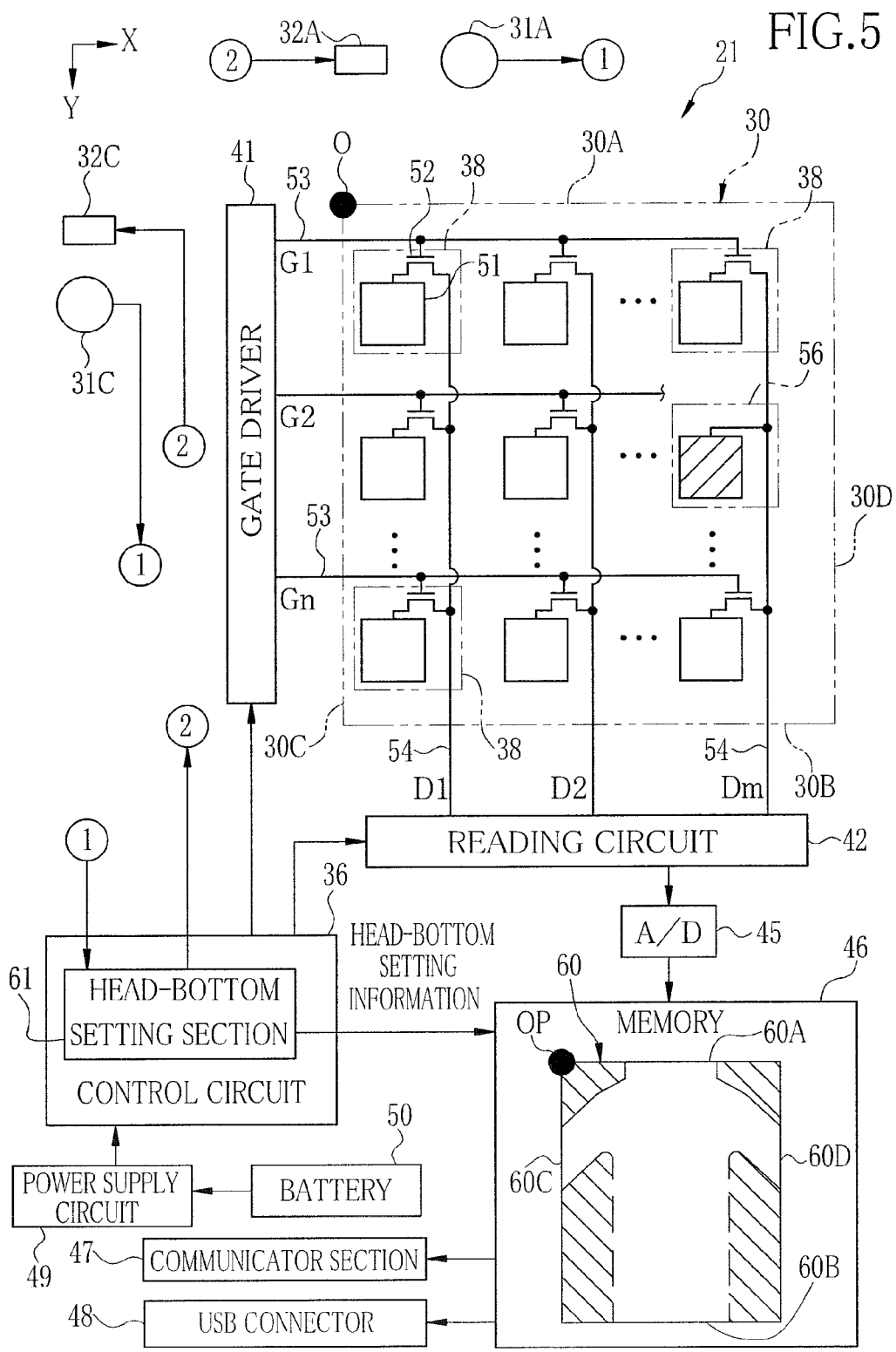
FIG. 5 is an explanatory diagram illustrating a sensor panel and a head-bottom setting section.

As shown in FIG. 5, the sensor panel 21 is provided with a thin film transistor (TFT) active matrix substrate with the imaging area 30 formed thereon, a gate driver 41, a reading circuit 42, a control circuit 36, an A/D converter 45, the memory 46, a communicator section 47, an USB connector 48, a power supply circuit 49 and a battery 50.

In the imaging area 30, a plurality of pixels 38 for accumulating signal charges according to the incident amount of X-rays are arranged at predetermined intervals in a matrix of N-lines (X-direction) and M-columns (Y-direction). Note that "N" and "M" represent plural integers, e.g., N, M=around 2000. The arrangement of the pixels 38 is not limited to a square matrix array, but may be a honeycomb array. The sensor panel 21 is of an indirect conversion type that has a scintillator (a not-shown phosphorous member) for converting X-rays to visible rays and converts the visible rays to electric charges through the pixels 38. The scintillator is made of a phosphor such as thallium-activated cesium iodide (CsI:Tl) or terbium-activated gadolium oxysulfide (GOS, Gd2O2S:Tb), and is positioned to face the whole imaging area 30. Note that the sensor panel 21 may also be of a direct conversion type using a conversion layer that converts X-rays directly to electric charges.

Each pixel 38 includes a photodiode 51 and a thin film transistor (TFT) 52 as a switching element. The photodiode 51 is a photoelectric conversion element that generates electric charges (electrons-positive holes) in response to incident visible rays and accumulates the generated electric charges. The TFT 52 is connected at the gate electrode to a scanning line 53, at the source electrode to a signal line 54, and at the drain electrode to the photodiode 51. The scanning lines and the signal lines 54 are arranged in a grid. The scanning lines 40 are provided for the respective rows of pixels 38 ("N" pixel lines), and the signal lines 54 are provided for the respective columns of pixels 38 ("M" pixel columns). The scanning lines 40 are connected to the gate driver 41, whereas the signal lines 54 are connected to the reading circuit 42.

The gate driver 41 drives the TFTs 52 under the control of the control circuit 36, to cause he 21 to make accumulating operations for accumulating the signal charges in the pixels 38 and reading operations for reading out the signal charges from the pixels 38. The gate driver 41 turns off the TFTs 52 of all pixels 38 during the X-ray irradiation, so that signal charges are accumulated in the pixels 38. After the X-ray irradiation is terminated, the gate driver 41 turns on the TFTs 52 line by line by inputting gate pulses G1 to Gn sequentially to the scanning lines 53, one gate pulse to one scanning line 53, thereby executing the signal charge reading operations. The signal charges read out from the pixels 38 are fed through the signal lines 54 into the reading circuit 42.

The reading circuit 42 reads out the signal charges D1 to Dm from the pixels 38. The control circuit 36 comprehensively controls the respective components. The A/D converter 45 converts the read signal charges to digital data.

The reading circuit 42 consists of an integrating amplifier for converting the signal charges read out from the pixels 38 to voltage signals, and a multiplexer for outputting the voltage signals line by line while sequentially switching the columns of the pixels 38 in the imaging area. In the reading operation, the voltage signals input in the reading circuit 42 are converted to digital data through the A/D converter 45 and then written as digital image data in the memory 46. The image data written in the memory 46 constitutes a frame of X-ray image 60.

A detective pixel 56 for detecting the start of X-ray irradiation is also provided in the imaging area 30. A part of the pixels 38 is utilized as the detective pixel 56, and like the ordinary pixels 38, the detective pixel 56 has the photodiode 51 but has no TFT 52, so that the photodiode 51 of the detective pixel 56 is short-circuited or connected directly to the signal lines 54. Accordingly, the output (signal charges generated from the photodiode 51) of the detective pixel 65 flow into the signal lines 54 regardless of whether the TFTs 52 of the pixels 38 are turned on or off.

The output of the detective pixel 56 is read through the reading circuit 42 and the A/D converter 45 into the memory 46, in the same way as for the pixels 38, but the reading operations from the detective pixel 56 are repeated at shorter intervals that are in the order of microseconds. The output of the detective pixel 56 obtained by one reading operation corresponds to the amount of incident X-rays per unit time. From the start of X-ray irradiation, the amount of incident X-rays per unit time will gradually increase, and the output of the detective pixel 56 will increase correspondingly.

The control circuit 36 reads the output of the detective pixel 56 each time the output is written on the memory 46 and compares the output of the detective pixel 56 with a predetermined start threshold value, to determine that the X-ray irradiation has started when the output reaches or exceeds the threshold. Thus, the sensor panel 21 can detect the start of X-ray irradiation by itself without the need for receiving a synchronizing signal from the X-ray generator (i.e. the round-visit vehicle 11 in this embodiment). Furthermore, because it is possible to read the output of the detective pixel 56 even during the accumulating operation of the sensor panel 21, the control circuit 36 can detect the end of X-ray irradiation on the basis of the output of the detective pixel 56.

When the start of X-ray irradiation is detected, the sensor panel 21 turns off the TFTs 52 of the pixels 38 to start the accumulating operation. The sensor panel 21 continues reading the output of the detective pixel 56 during the accumulating operation. The control circuit 36 determines that the X-ray irradiation is terminated when the read output decreases to a predetermined end threshold value or less.

After detecting the end of X-ray irradiation, the reading operation is carried out to write the X-ray image 60 in the memory 46. The origin point OP of the X-ray image 60 in the memory 46 corresponds to the origin O of the imaging area 30, and four sides 60A, 60B, 60C and 60D of the X-ray image 60 correspond to the four sides 30A, 30B, 30C and 30D of the imaging area 30, respectively. The memory 46 is capable of storing multiple frames of X-ray images 60.

The control circuit 36 is provided with a head-bottom setting section 61. The head-bottom setting section 61 receives the operation command entered through the first operation button 31A or the second operation button 31C, to set either the first short side 30A or the first long side 30C of the imaging area 30 to be the head of the X-ray image 60 in the display orientation. The head-bottom setting section 61 is connected to the first operation button 31A, the second operation button 31C, the first lamp 32A and the second lamp 32C. The head-bottom setting section 61 turns the first lamp 32A on and the second lamp 32C off while the first operation button 31A is on, or turns the second lamp 32C on and the first lamp 32A off while the second operation button 31C is on.

Figure 6:
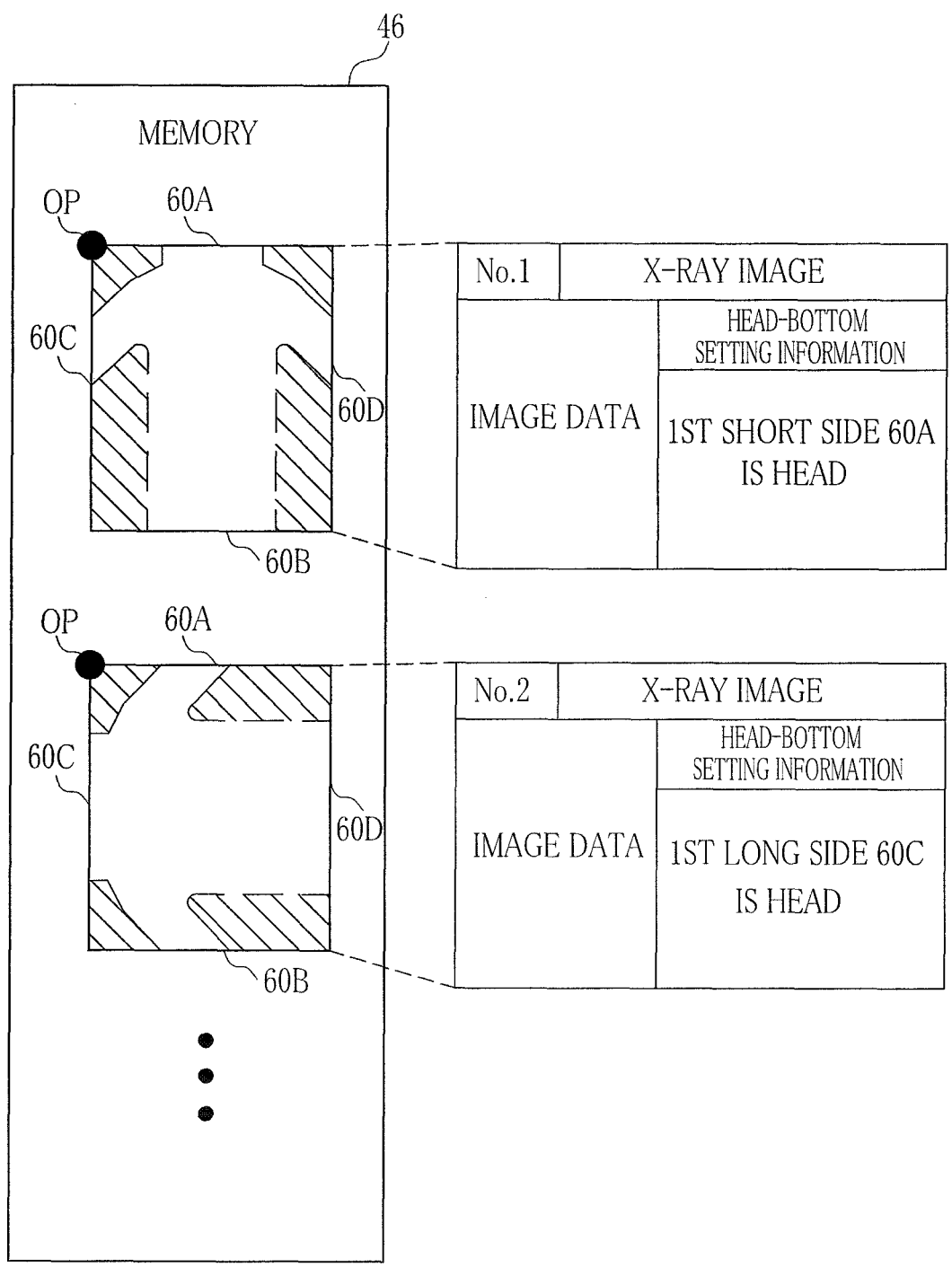
FIG. 6 is an explanatory diagram illustrating the storage of X-ray images in a memory in association with head-bottom setting data.

As shown in FIG. 6, the head-bottom setting section 61 stores information on the head-bottom setting, which determined by the operation command from the first operation button 31A or the second operation button 31C, in association with the X-ray image 60 in the memory 46. The head-bottom information is associated with the X-ray image 60, for example, by attaching the head-bottom information as additional information to the image data. When the first short side 30A is set to be the head, the head-bottom setting section 61 records such head-bottom information that indicates that the first short side 60A corresponding to the first short side 30A of the imaging area 30 is the head of the image in association with each X-ray image that is read out under this setup condition, as shown with respect to an X-ray image 60 numbered #1 in FIG. 6. On the contrary, when the first long side 30C is set to be the head, such head-bottom information that indicates that the first long side 60C corresponding to the first long side 30C of the imaging area 30 is the head of the image is recorded in association with each X-ray image that is read out under this setup condition, as shown with respect to an X-ray image 60 numbered #2.

Referring back to FIG. 5, the communicator section 47 is for transmitting the X-ray images 60 stored in the memory 46 to an external device. For example, the communicator section 47 is a wireless communicator section that has an antenna and is able to transmit the X-ray images 60 wirelessly. The USB connector 48 is a connector for connecting an USB (universal serial bus) cable, so that the X-ray images 60 may be transmitted through the USB cable to an external device. The power supply circuit 49 supplies power from the battery 50 to the sensor panel 21, the control circuit 36, etc. The power supply circuit 49 mainly consists of a DC/DC converter for converting the voltage of the DC power from the battery 50 to a value determined depending on the device to be supplied.

Figure 7:
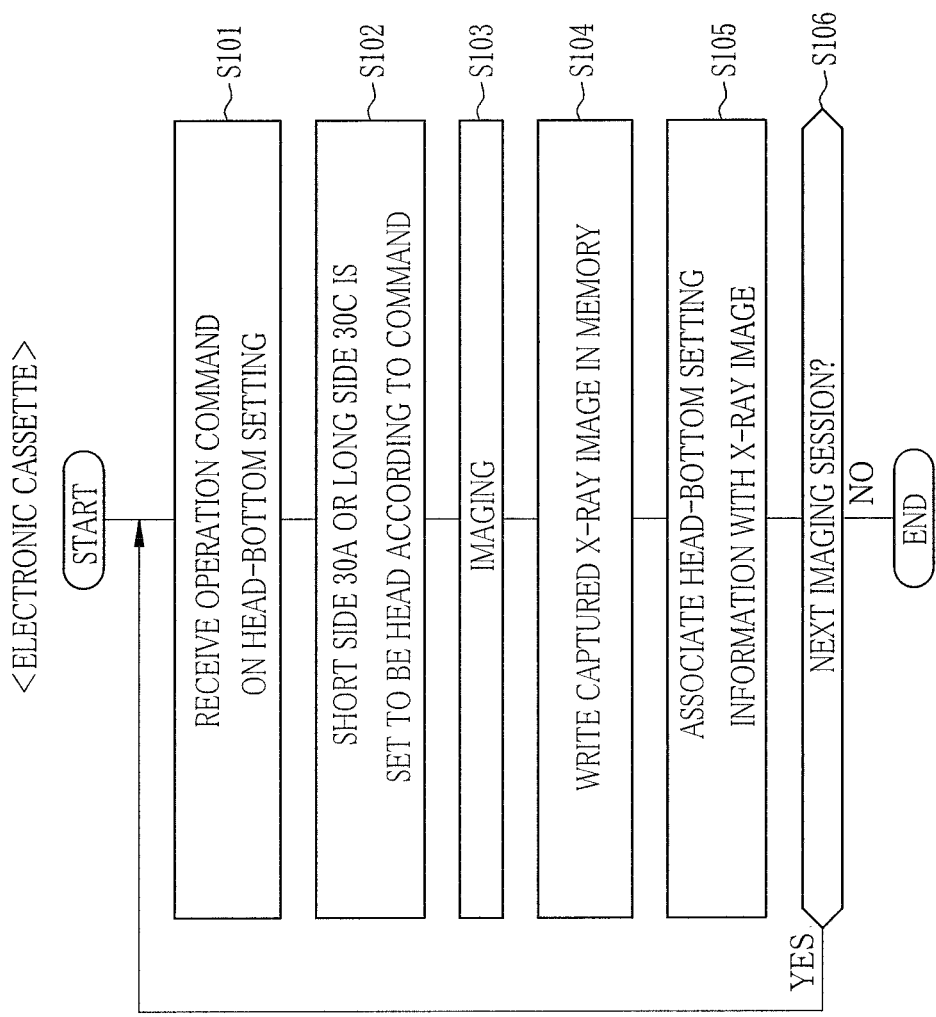
FIG. 7 is a flowchart showing the sequence of using the electronic cassette.
Figure 8:
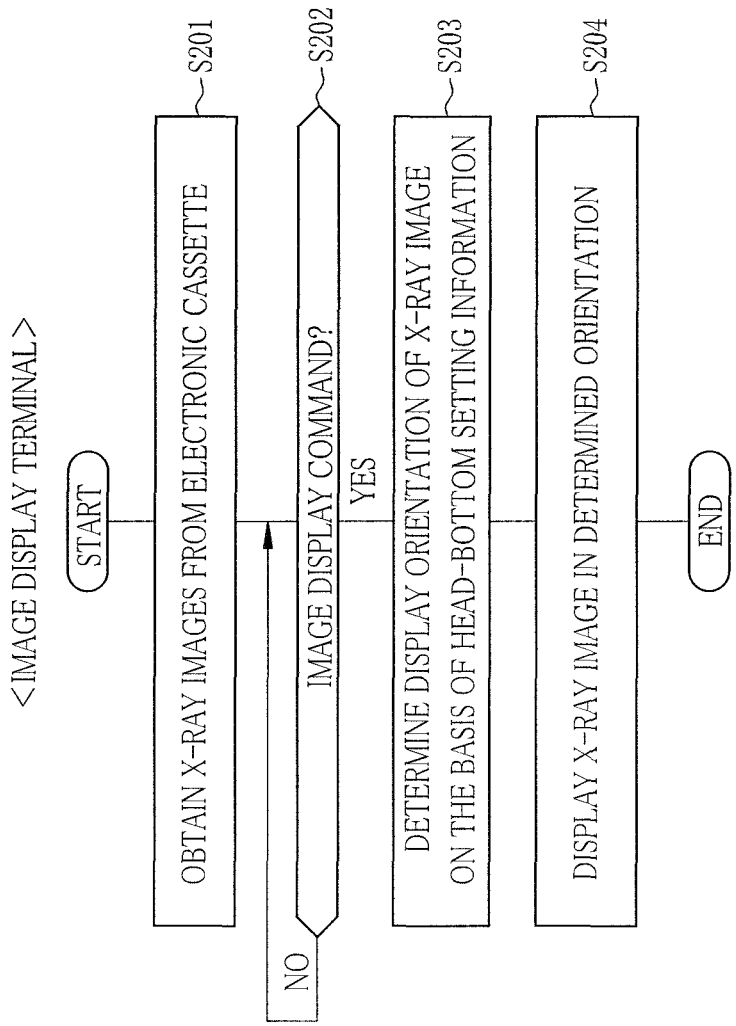
FIG. 8 is a flowchart showing the sequence of displaying an X-ray image on an image display terminal.
Figure 9:
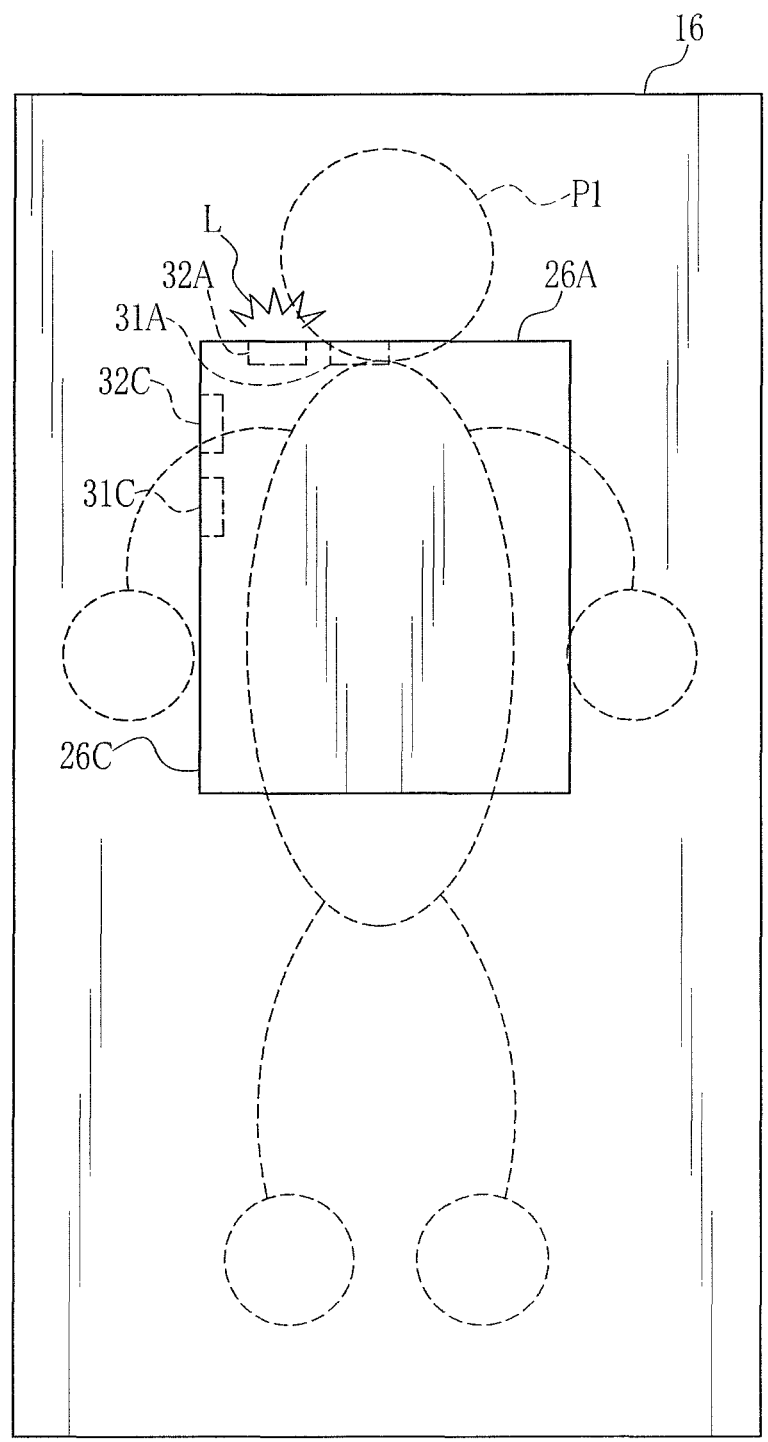
FIG. 9 is an explanatory diagram illustrating an arrangement of the electronic cassette in a case having an average body width.

The operation of the above configuration will be described with reference to the flowcharts in FIGS. 7 and 8 and the explanatory diagrams in FIGS. 9 to 11. When making a round-visit radiography, a radiologist T puts the electronic cassette 10 in the cassette container 14A of the round-visit vehicle 11 and goes to the medical ward where the patient T to be imaged stays. In the medical ward, the electronic cassette 10 is positioned to the imaging site of the patient P, and the X-ray source 12 is adjusted to face the electronic cassette 10, as shown in FIG. 1.

When positioning the electronic cassette 10, the radiologist T operates the first operation button 31A or the second operation button 31C to enter the command for setting the head and bottom in the display orientation of the X-ray image 60. For example, as shown in FIG. 9, when imaging the chest of a patient P1 who has an average trunk width, the electronic cassette 10 may be positioned in the vertically-long orientation, setting the first short side 30A at the head, so as to cover the chest, the imaging subject, within the range of the imaging area 30. In this case, the first operation button 31A is pushed down to set the first short side 30A to be the head of the image, or if the first short side 30A is initially set to be the head margin, it is unnecessary to operate either of the first operation button 31A and the second operation button 31C.

While the first short side 30A is being set to be the head margin, the first lamp 32A disposed on the corresponding side surface 26A to the first short side 30A is kept on, so that it is possible to confirm from the outside of the housing 23 which side is set to be the head margin.

Figure 10:
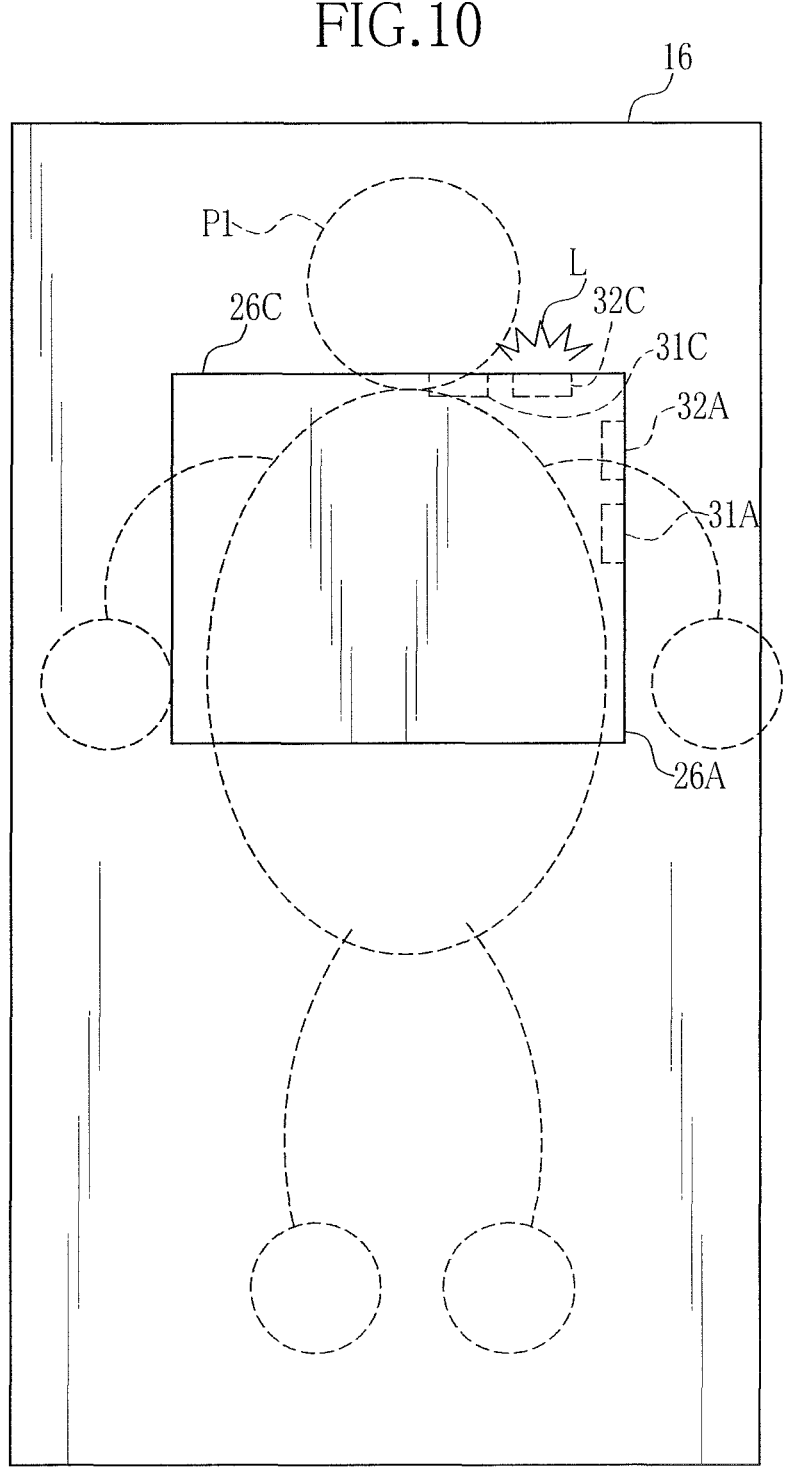
FIG. 10 is an explanatory diagram illustrating an arrangement of the electronic cassette in a case having a wider body width than average.
Figure 11:
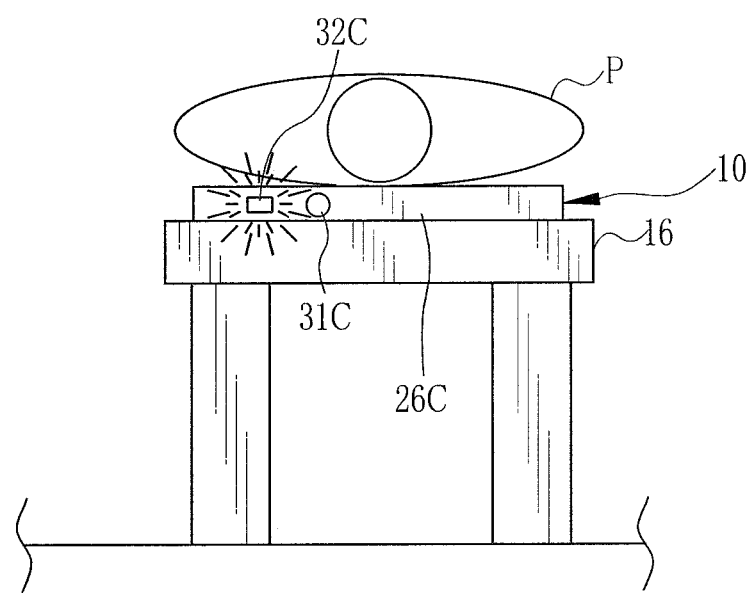
FIG. 11 is an explanatory diagram illustrating the visibility of light from a lamp from one side of the electronic cassette.

Meanwhile, when imaging the chest of a patient P2 who has a wider trunk width than average, as shown in FIG. 10, if the electronic cassette 10 is positioned in the vertically-long orientation, setting the first short side 30A at the head to the patient P2, the chest to be imaged may not be covered within the range of the imaging area 30. In that case, the electronic cassette 10 is positioned in the horizontally-long orientation, setting the first long side 30C at the head to the patient P2, and the second operation button 31C is pushed down to set the first long side 30C to be the head margin of the image. By pushing down the second operation button 31C, the second lamp 32C disposed on the side surface 26C corresponding to the first long side 30C is turned on, so that it is possible to confirm that the first long side 30C is set to be the head margin.

There may also be such cases where the orientation of the electronic cassette 10 to the patient is limited by circumferential conditions in the medical ward or patients bedroom. In those cases, the head and bottom in the image display orientation can be set by operating the first operation button 31A or the second operation button 31C according to the selectable orientation of the electronic cassette 10.

Referring back to FIG. 7, when the operation command relating to the head-bottom setting is entered, the electronic cassette 10 accepts the entered operation command (S101). Then the first short side 30A or the first long side 30C is set to be the head margin according to the operation command. The head-bottom setting may be made before or after the cassette positioning. As shown in FIG. 11, since the first operation button 31A and the second operation button 31C are provided on the side surfaces 26 of the housing 23, it is possible to access these buttons through the gap between the patient P and the bed 16 while the electronic cassette 10 is inserted in between the patient P and the bed 16. Also the first lamp 32A and 32C are provided on the side surfaces 26, the light L from the first lamp 32A or the second lamp 32C is visible through the gap between the patient P and the bed 16.

Thus, the electronic cassette 10 facilitates the head-bottom setting in the display orientation of the X-ray image 60 just by operating the first operation button 31A or the second operation button 31C. Since no cable nor console is necessary for the head-bottom setting, it is not only very simple but also enables a round-visit radiography without the need for carrying a console along with the electronic cassette 10. Film cassettes and IP (imaging plate) cassettes, which have been used as conventional X-ray image recording media, need not use any console. The electronic cassette 10 in accordance with the present invention can be conveniently used in the same way as the film cassettes and the IP cassettes.

After positioning the electronic cassette 10, the conditions for an irradiation, including the tube voltage and tube current of the X-ray source 12 and the irradiation time, are set up. Thereafter when the activator switch 15 is operated, the X-ray source 12 starts radiating X-rays. As having the function to detect the start of X-ray irradiation, the electronic cassette 10 detects the start of irradiation upon being irradiated with the X-rays, and then switches to the accumulating operation to capture an X-ray image 60 (S103). Upon detecting the end of irradiation, the electronic cassette 10 switches to the reading operation to write the read X-ray image 60 in the memory 46 (S104). The head-bottom setting section 61 writes the head-bottom setting information in association with the X-ray image 60 (S105). The X-ray image 60 is stored in the memory 46.

If the next cession of imaging is required ("YES" in step S106), the same procedures as above are repeated. If not (("NO" in step S106), the imaging is terminated. After the imaging of the patient P is accomplished, the round-visit vehicle 11 is moved to the next bed or bedroom to restart imaging of the next patient P. In the next patients bedroom, the head-bottom setting is performed as required. The head-bottom setting information is associated with each X-ray image 60. Because the memory 46 can store multiple X-ray images 60, one electronic cassette 10 may serve for imaging a number of patients P.

After accomplishing the round-visit radiography, the radiologist T returns to a standby room. The radiologist T checks the X-ray images 60 captured through the round-visit radiography while displaying the images on an image display terminal such as a console. In this case, as shown in FIG. 8, the image display terminal obtains the X-ray image 60 from the electronic cassette 10 (S210). When an image display command for displaying the X-ray image 60 is input to the image display terminal (S202), the image display terminal determines the display orientation of each X-ray image 60 on the basis of the head-bottom setting information that is associated with the individual X-ray image 60 (S203). If necessary, turning process of the X-ray image 60 is automatically carried out to display the X-ray image 60 in the determined display orientation (S204).

Thus, if the X-ray image 60 is captured in the vertically-long orientation, the X-ray image 60 is displayed with the first short side 60A thereof at the head. If the X-ray image 60 is captured in the horizontally-long orientation, the X-ray image 60 is displayed with the first long side 60C thereof at the head. Therefore, it is unnecessary for the radiologist T to change the display orientation, reducing the labor of the radiologist T. Especially for such round-visit radiography that does not use a console and stores a lot of X-ray images 60 in the memory 46 of the electronic cassette 10, the feature of making it unnecessary to manually change the display orientation afterward is advantageous. There may be such X-ray images 60 that contain those subjects which are difficult to visually determine the head and bottom thereof. In those cases, it is difficult to determine the head and bottom of the subject of the X-ray image 60 on the display and correctly change the display orientation of the X-ray image 60. The present invention allows the head-bottom setting in the field of imaging with reference to the position of the electronic cassette 10 to the subject, and by associating the head-bottom setting information with the X-ray image 60, the present invention ensures checking the X-ray image 60 quickly in the proper display orientation.

The X-ray image 60 captured by the electronic cassette 10 may also be uploaded to the image server 17, from which the X-ray image 60 can be downloaded to the terminal 20 of the diagnosis and treatment department 19 that has ordered the radiography. In that case, the terminal 20 can automatically change the display orientation of the X-ray image 60 on the basis of the head-bottom setting information. Therefore the doctor D who observes the X-ray image 60 does not need to change the display orientation.

A method of determining the display orientation of the X-ray image 60 automatically by analyzing the X-ray image 60 to recognize the posture of the subject in the X-ray image 60 is known. However, the method based on the image analysis involves the risk of determination errors due to insufficient accuracy. The head-bottom setting by operating the first operation button 31A or the second operation button 31C in accordance with the present invention makes it possible to determine the display orientation exactly in comparison with the determination method based on the image analysis.

Figure 12:
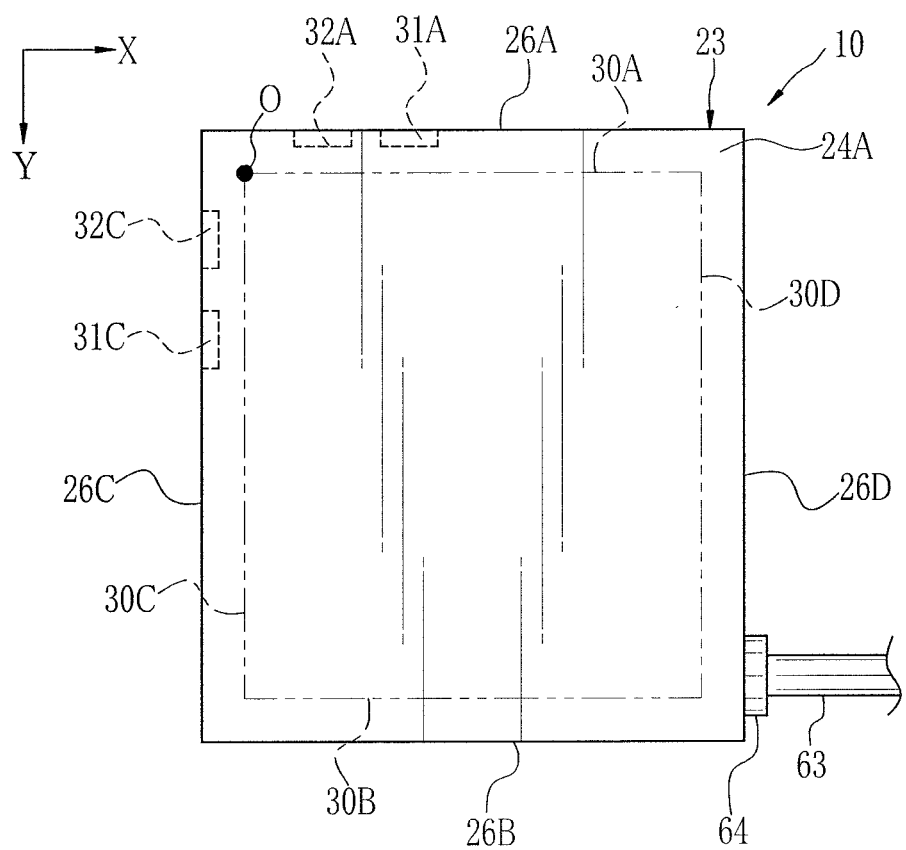
FIG. 12 is a schematic plan view of an electronic cassette having a cable connector.

The present embodiment has been described with respect to an example where the electronic cassette 10 is of a wireless type that has the wireless communicator section 47 and can be driven by the power from the battery 50. The present invention is also applicable to an electronic cassette 10 that is provided with a cable connector 64 for connecting a cable 63 to the electronic cassette 10, as shown in FIG. 12. The cable 63 is, for example, a composite cable for power supply from a commercial power source and for wired communication. Providing the cable connector 64 makes it possible to drive the electronic cassette 10 through the cable 63 when the battery 50 has run down in the middle of the round-visit radiography. Furthermore, after completing the round-visit radiography, the X-ray image 60 stored in the electronic cassette 10 may be transmitted to an external device through the cable 63.

The cable connector 64 may also be used for synchronized communication between the round-visit vehicle 11 and the source controller unit 13. Since the electronic cassette 10 has the facility to detect the start of X-ray irradiation, communication for synchronization with the source controller unit 13 is not required. However, for an electronic cassette that has no facility to detect the start of X-ray irradiation, communication for synchronization with the source controller unit 13 is necessary in order to control the operation of the sensor panel 21 in synchronism with the start of radiation from the X-ray source 12. Therefore, the cable connector 64 and the cable 63 may be used for the communication with the source controller unit 13.

Figure 13:
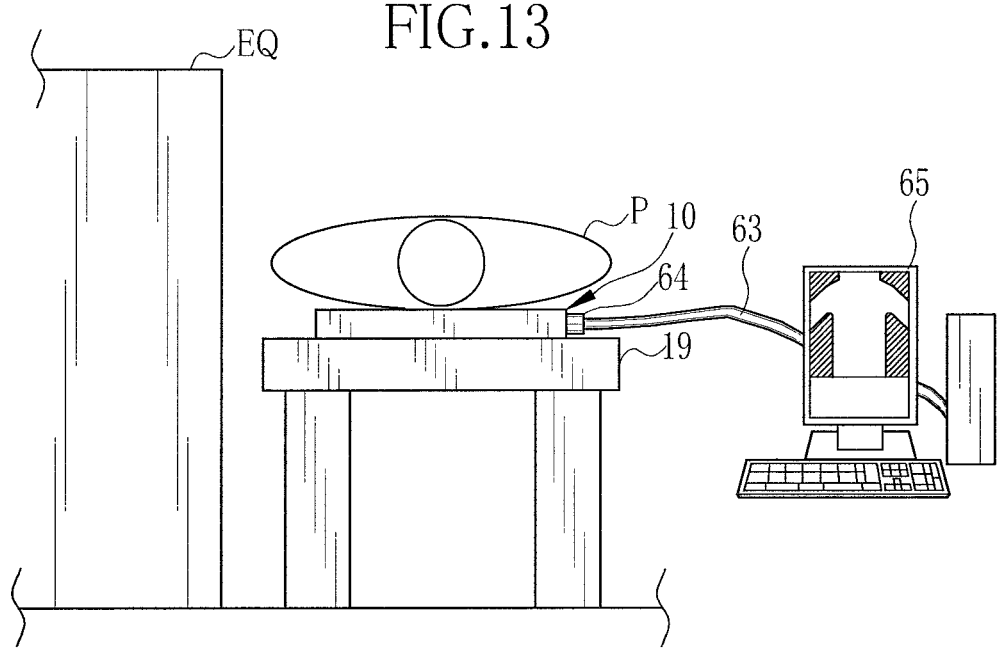
FIG. 13 is an explanatory diagram illustrating the wiring of a cable to the electronic cassette of FIG. 12.

Furthermore, the present embodiment has been described with respect to a round-visit radiography that is performed without carrying a console, the electronic cassette 10 having the cable connector 64 may be used for a round-visit radiography that is performed while carrying a console with the electronic cassette 10. In this case, as shown in FIG. 13, the electronic cassette 10 is connected to a console 65 through the cable connector 64 and the cable 63 so as to communicate with the console 65.

When the electronic cassette 10 is used with the cable 63 connected thereto, it is necessary to set the cable 63 properly according to the position of the electronic cassette 10. In some cases, it is required to change the drawing direction of the cable 63 from the electronic cassette 10. However, as shown in FIG. 13, the drawing direction of the cable 63 can be limited by equipment EQ in a patients bedroom. In that case, the position of the electronic cassette 10 should be determined by the drawing direction of the cable 63. Then there may be cases where the initial setting on the head-bottom direction of the electronic cassette 10 does not correspond to the head-bottom direction of the subject. In those cases, the head-bottom setting function using the operation buttons 31A and 31C is convenient because it is possible to record the head-bottom setting information for each X-ray image. Thus, not only in the case using no cable 63 but also in the case using the cable 63, the head-bottom setting function of the electronic cassette 10 in accordance with the present invention exhibits a prominent effect. Accordingly, the present invention is applicable to an electronic cassette of a wired type having a wired communicator section.

In the present embodiment, the first operation button 31A, the second operation button 31C, the first lamp 32A and the second lamp 32C are provided on the frame 28 of the front housing 24. Forming the frame 28 from plastics makes it easy to process the frame 28 for assembling the first and second operation buttons 31A and 31C and the first and second lamps 32A and 32C. Therefore, the operation buttons 31A and 31C and the lamps 32A and 32C are preferably provided on the plastic frame 28 as compared to the metal rear housing 25. Since the frame 28 is located on the periphery of the housing 23, it is better to dispose the operation buttons 31A and 31C and the lamps 32A and 32C on the frame 28 in view of operability and visibility.

In the present embodiment, the operation buttons 31A and 31C and the lamps 32A and 32C are disposed on the side surfaces 26 of the housing 23. In an alternative, the operation buttons 31A and 31C and the lamps 32A and 32C may be disposed in a portion of the frame 28, which is on the front surface 24A. Because the operation for setting the head and bottom is considered to be often made prior to the positioning of the electronic cassette 10 to the patient P, the necessity of locating the operation buttons 31A and 31C on the side surfaces 26 is not so great when taking consideration of the operability after the positioning. Therefore, the operation buttons 31A and 31C may be provided in other locations than the side surfaces 26, e.g. on the margins of the front surface 24A. The lamps 32A and 32C may also be provided in other locations than the side surfaces 26. However, because it is preferable to dispose the lamps 32A and 32C in such a location where the lamps 32A and 32C are visible after the positioning of the electronic cassette 10, the necessity of locating the lamps 32A and 32C on the side surfaces 26 is greater in comparison with the operation buttons 31A and 31C.

Second Embodiment

Figure 14:
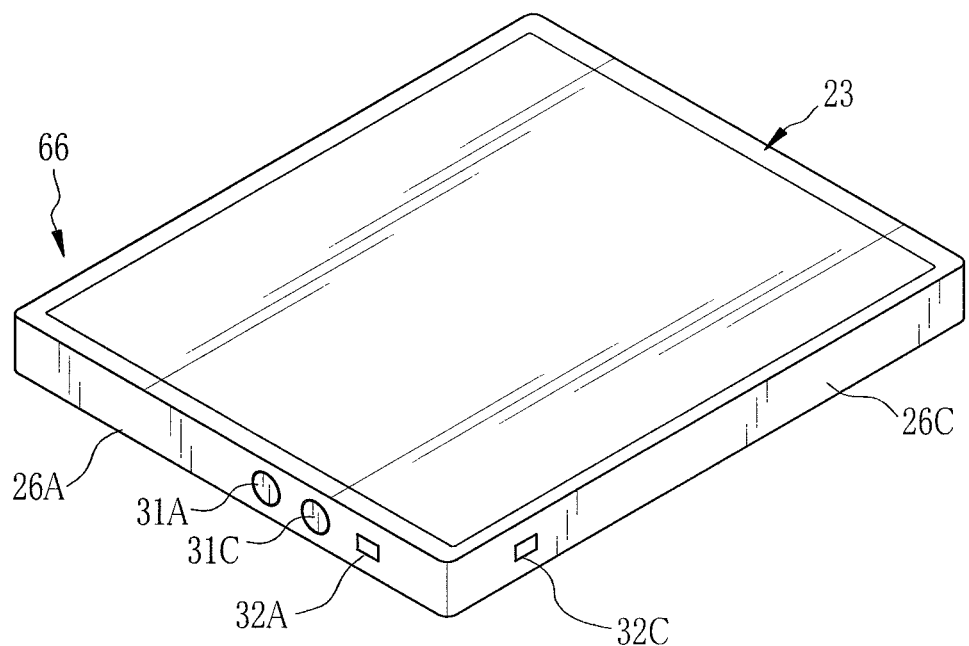
FIG. 14 is a diagrammatic perspective view of an external appearance of an electronic cassette in an aspect of a second embodiment.
Figure 15:
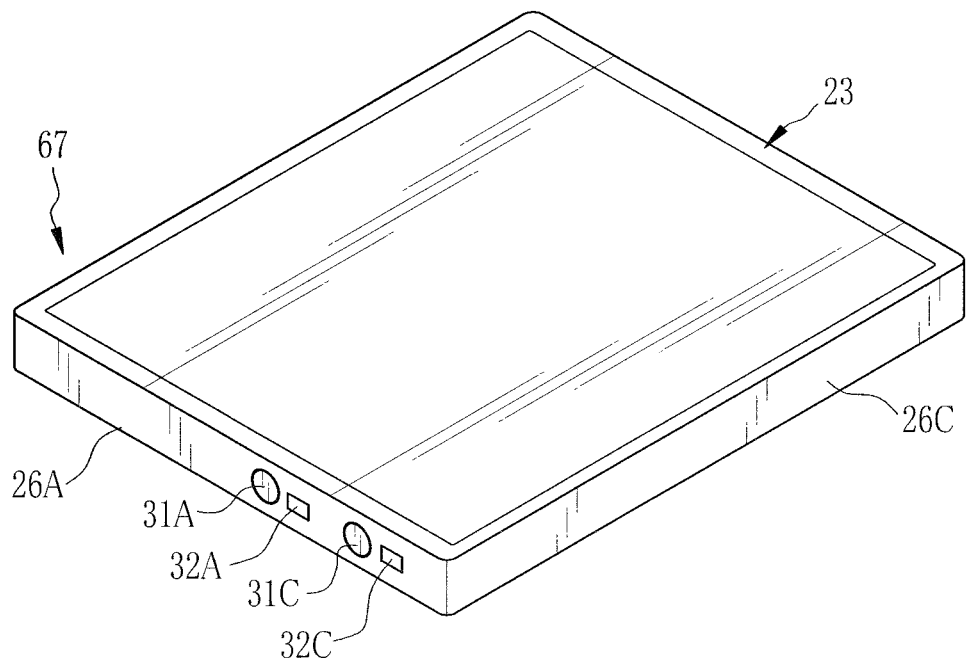
FIG. 15 diagrammatic perspective view of an external appearance of an electronic cassette in another aspect of the second embodiment.

In the first embodiment, the first and second operation buttons 31A and 31C are disposed respectively on the side surfaces 26A and 26C that correspond to the first short side 30A and the first long side 30C of the imaging area 30, which adjoin each other. It is alternatively possible to dispose the first and second operation buttons 31A and 31C on one side surface of the housing 23. FIGS. 14 and 15 show examples of electronic cassettes 66 and 67 that have the first and second operation buttons 31A and 31C disposed on one side 26A in accordance with the second embodiment. In the electronic cassette 67 shown in FIG. 15, the first and second lamps 32A and 32C are also disposed on the one side 26A. In this example, it is preferable to provide markers beside the lamps 32A and 32C so as to indicate the correspondence of the lamps 32A and 32C to the first short side 30A and the first long side 30C. Other than the above aspect, the second embodiment may have the same features as the first embodiment.

Third Embodiment

Figures 16, 17:
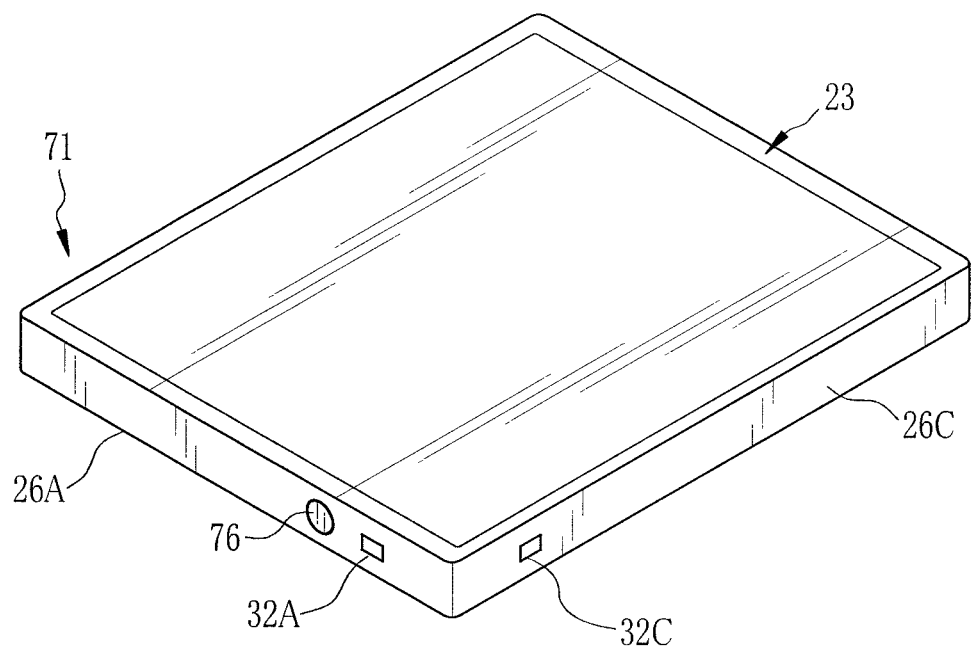
FIG. 16 is a diagrammatic perspective view of an external appearance of an electronic cassette of a third embodiment.
FIG. 17 is an explanatory diagram illustrating the head-bottom setting data in the electronic cassette of FIG. 16.

In accordance with the third embodiment shown in FIGS. 16 to 20, electronic cassettes 71, 72 and 73 are provided with a single operation button for inputting operation commands. Except the features relating to the operation button and lamps, the third embodiment may have the same features as the first embodiment, so that the following description will be focused on the differences from the first embodiment. The electronic cassette 71 differs from the first embodiment in that an operation button 76 is disposed only on a side surface 26A but not on a side surface 26C. The operation button 76 is a push button that is alternatively turned on and off upon each pushdown operation. The correlations between the ON/OFF of the operation button 76, the ON/OFF of a first lamp 32A, the ON/OFF of a second lamp 32C, and the head-bottom setting information in the electronic cassette 71 are shown in FIG. 17.

While the operation button 76 is off, the first lamp 32A is on, the second lamp 32C is off, and the head-bottom setting information, which will be associated with an image captured in this condition, indicates that the first short side 60A of the image should be the head margin. When the operation button 76 is turned on, the first lamp 32A is turned off and the second lamp 32C is turned on, whereby the associated head-bottom setting information indicates that the first long side 60C should be the head margin. Thus, only with the operation button 76, it is possible to select either the short side or the long side to be the head margin of the image. Also it is possible to confirm the selected head-bottom direction from the alternative ON/OFF of the lamps 32A and 32C.

Figures 18, 19:
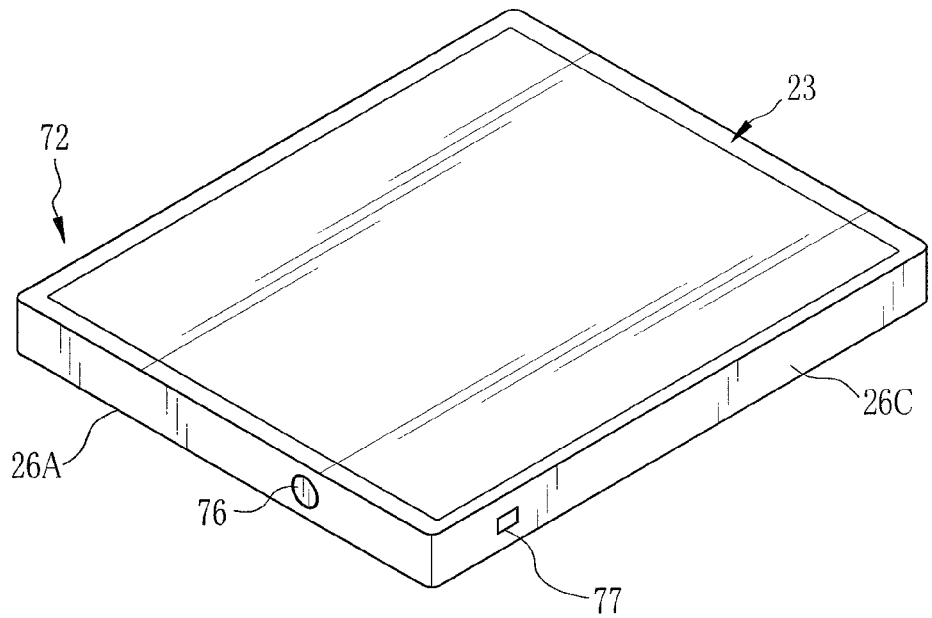
FIG. 18 is a diagrammatic perspective view of an external appearance of an electronic cassette in another aspect of the third embodiment.
FIG. 19 is an explanatory diagram illustrating the head-bottom setting data in the electronic cassette of FIG. 18.

FIG. 18 shows an example of the electronic cassette 72 which has merely an operation button 76 and a lamp 77. The correlations between the ON/OFF of the operation button 76, the ON/OFF of the lamp 77 and the head-bottom setting information in the electronic cassette 72 are shown in FIG. 19. That is, while the operation button 76 is off, the lamp 77 is off, and the head-bottom setting information indicates that the first short side 60A should be the head margin. While the operation button 76 is on, the lamp 77 is on, and the head-bottom setting information indicates that the first long side 60C should be the head margin.

Figure 20:
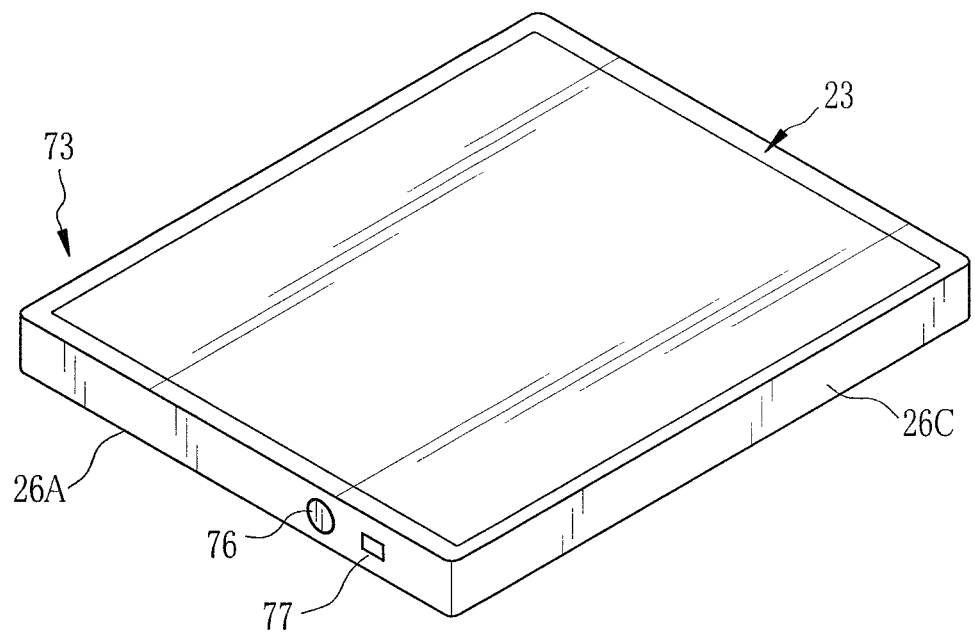
FIG. 20 is a diagrammatic perspective view of an external appearance of an electronic cassette in a further aspect of the third embodiment.

Alternatively, as shown in the electronic cassette 73 of FIG. 20, the operation button 76 and the lamp 77 may be disposed on one side 26A. Other features of the electronic cassette 73 may be equal to those of the electronic cassette 72.

Fourth Embodiment

In accordance with the fourth embodiment shown in FIGS. 21 to 25, any of four sides 30A to 30D of an imaging area 30 can be selected to be the head margin of the image.

Figure 21:
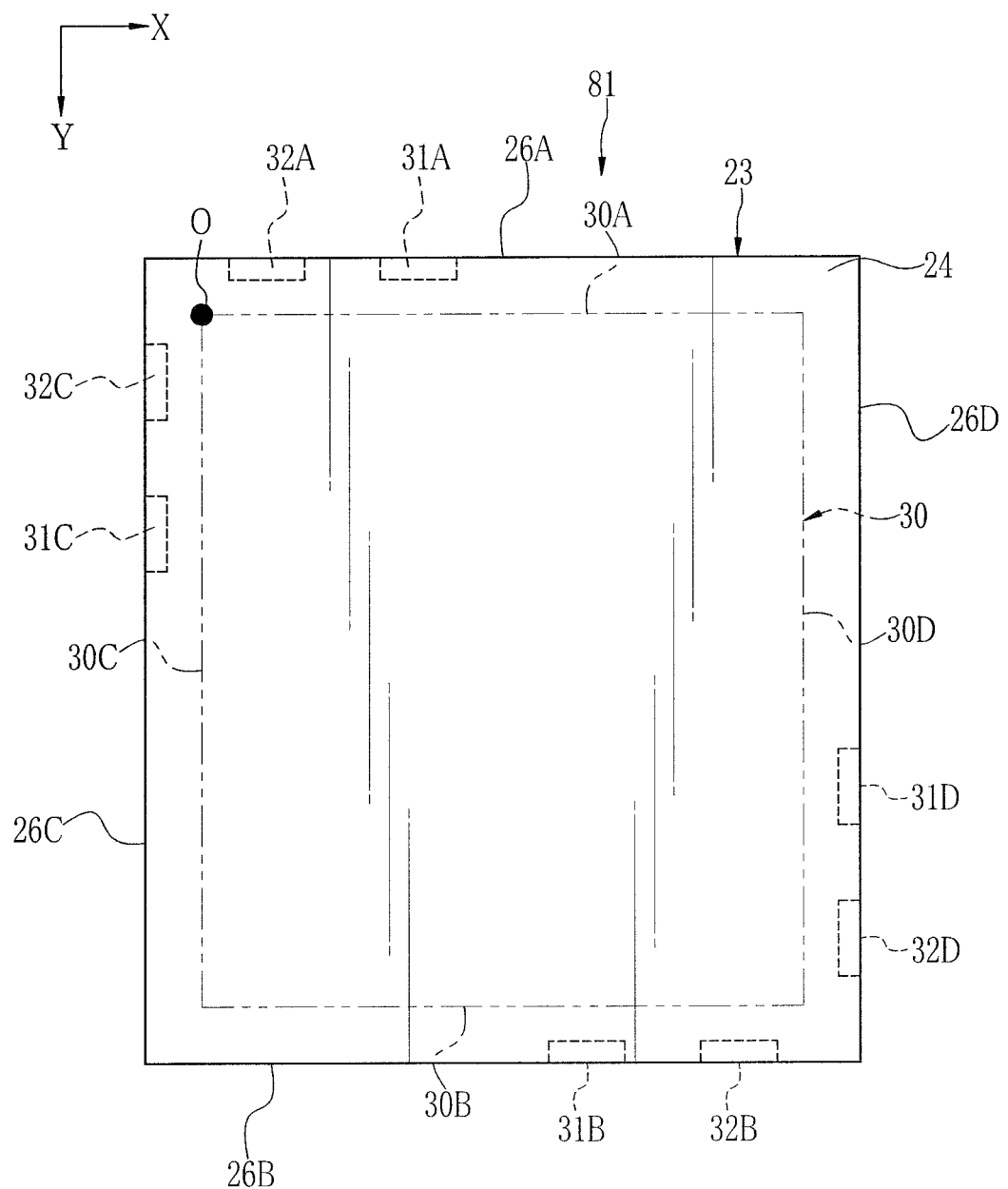
FIG. 21 is a schematic plan view of an external appearance of an electronic cassette of a fourth embodiment.
Figure 22:
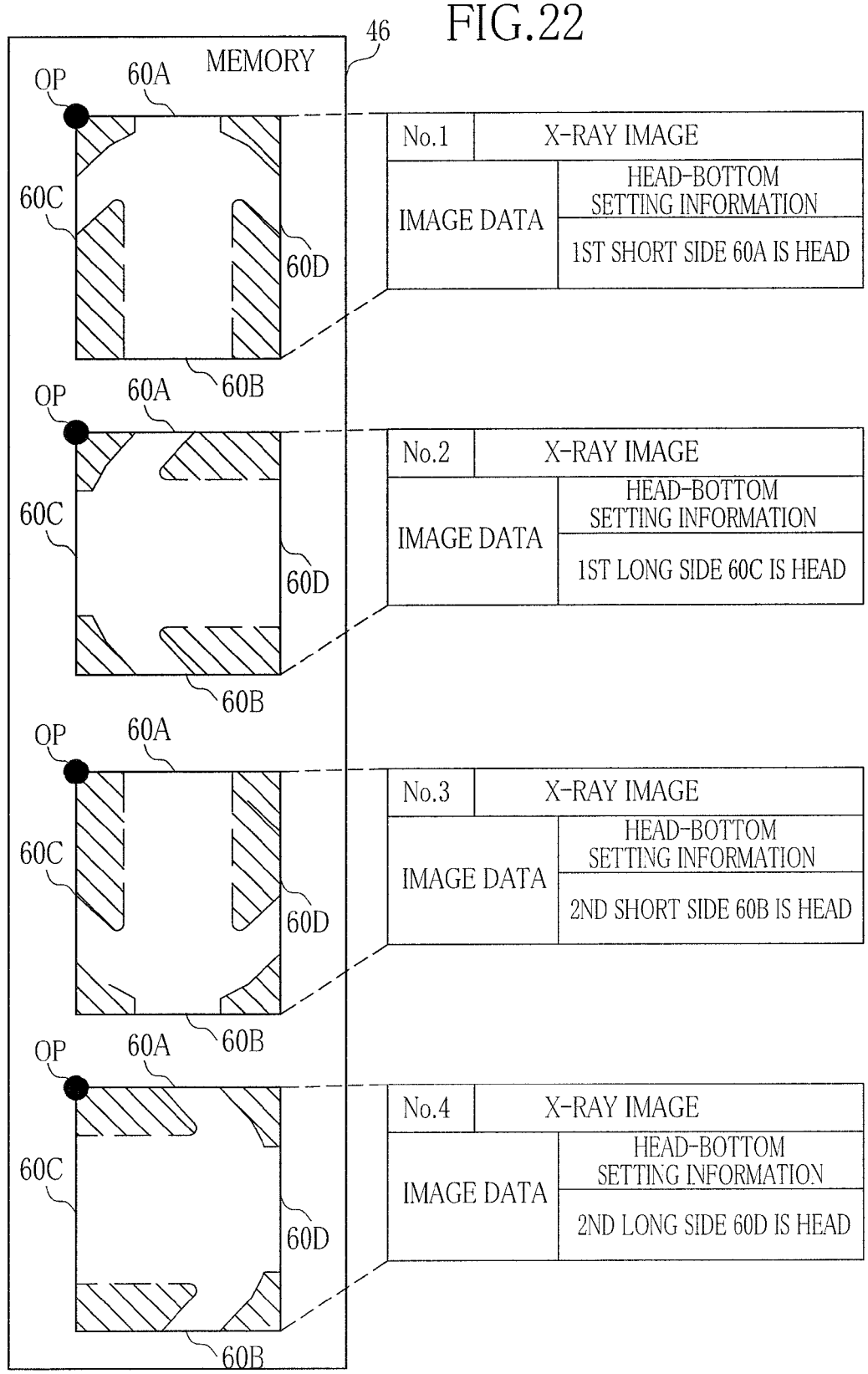
FIG. 22 is an explanatory diagram illustrating the head-bottom setting data in the electronic cassette of FIG. 21.
Figure 23:
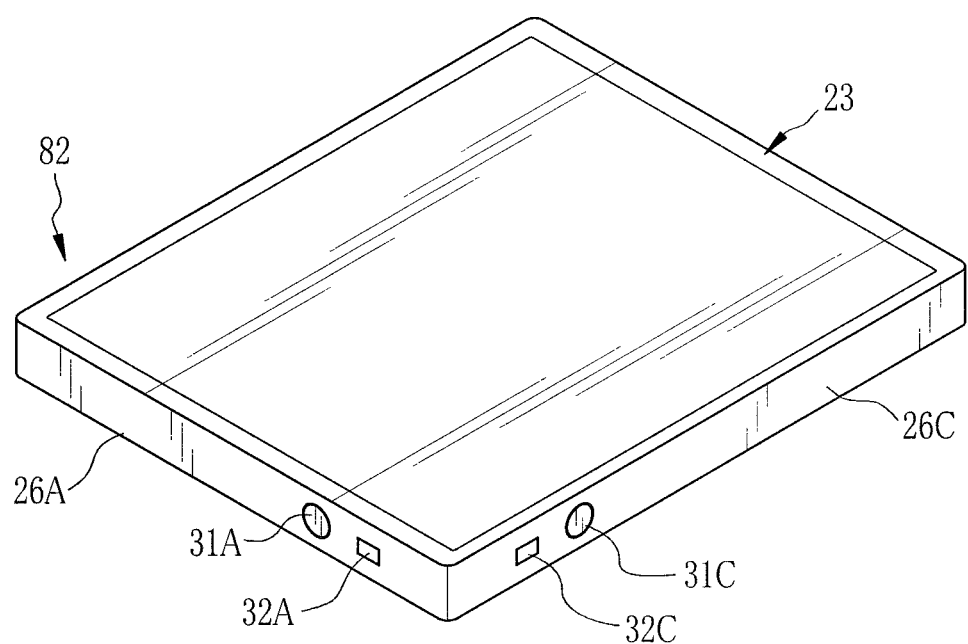
FIG. 23 is a diagrammatic perspective view of an external appearance of an electronic cassette in another aspect of the fourth embodiment.

In an electronic cassette 81 shown in FIG. 21, first to fourth operation buttons 31A to 31D and first to fourth lamps 32A to 32D are provided on four side surfaces 26A to 26D of a housing 23, which correspond to the four sides 30A to 30D of the imaging area 30, respectively. When any of the operation buttons 31A to 31D is pushed down, one of the first short side 30A to 30D that corresponds to the pushed operation button is set to be the head margin. At the same time, one of the lamps 32A to 32D that is disposed on the same side as the pushed operation button is turned on.

In this embodiment, head-bottom setting information associated with each X-ray image 60 will designate one of four display orientations: a first short side 60A, a second short side 60B, a first long side 60C or a second long side 60D of the X-ray image 60 should be the head margin. In the example illustrated in FIG. 22, the head-bottom setting information associated with an X-ray image 60 that is numbered #1 designates the first short side 60A to be the head margin, whereas the head-bottom setting information associated with a second X-ray image 60 that is numbered #2 designates the first long side 60C to be the head margin. A third X-ray image 60 that is numbered #3 is set to have the second short side 60B at the head, whereas a fourth X-ray image 60 that is numbered #4 is set to have the second long side 60D at the head. On the basis of the head-bottom setting information associated with each X-ray image 60, the display direction turning process is executed, as needed, on the X-ray image 60 at an image display terminal.

The fourth embodiment, wherein the head margin of the image can be set on any of the four sides of the imaging area, is not limited to the configuration of the electronic cassette 81 shown in FIG. 21, which has one operation button and one lamp on each of the four side surfaces 26A to 26D of the housing 23. For example, as shown in an electronic cassette 82 of FIG. 23, one operation button 31A or 31C and one lamp 32A or 31C may be disposed on each of adjoining two sides 26A and 26C of a housing 23, like in the electronic cassette 10 in accordance with the first embodiment.

The correlations between the ON/OFF of the operation buttons, the ON/OFF of the lamps, and the head-bottom setting information are shown in FIG. 24. If both the first and second operation buttons 31A and 31C are off, both the first and second lamps 32A and 32C are off. In this condition, the head-bottom setting information designates that the first short side 60A should be the head margin. In the second condition where the first operation button 31A is on and the second operation button 31C is off, the first lamp 32A is on and the second lamp 32C is off, and the head-bottom setting information designates that the first long side 60C should be the head margin.

In the third condition where the first operation button 31A is off and the second operation button 31C is on, the first lamp 32A is off and the second lamp 32C is on, and the head-bottom setting information designates that the second short side 60B should be the head margin. In the fourth condition where both the first and second operation buttons 31A and 31C are on, both the first and second lamps 32A and 32C are on, and the head-bottom setting information designates that the second long side 60D should be the head margin. Thus, it is possible to select the display orientation from among the four choices and indicate the selected head-bottom setting merely with the two operation buttons and the two lamps.

Figure 25:
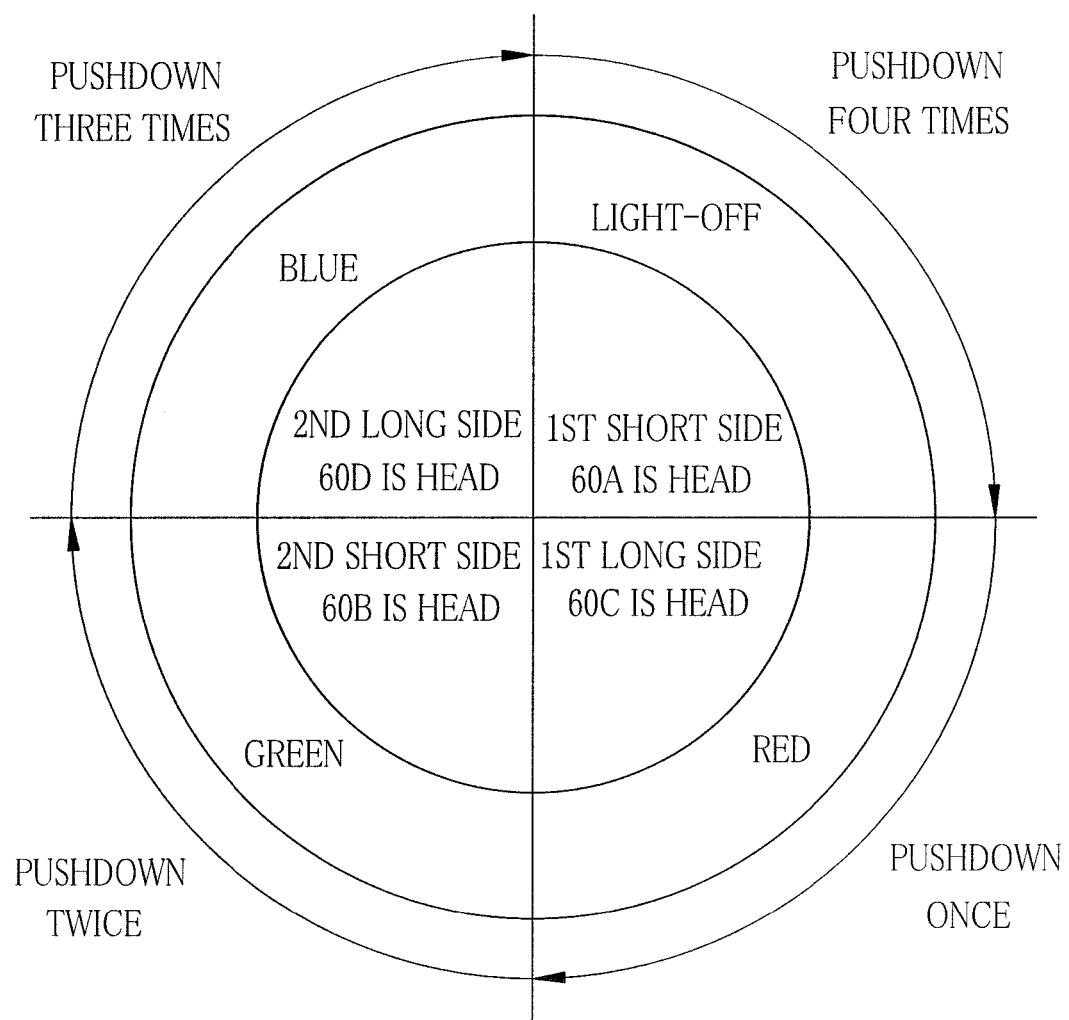
FIG. 25 is an explanatory diagram illustrating the head-bottom setting data in an electronic cassette in a further aspect of the fourth embodiment.
Figure 26:
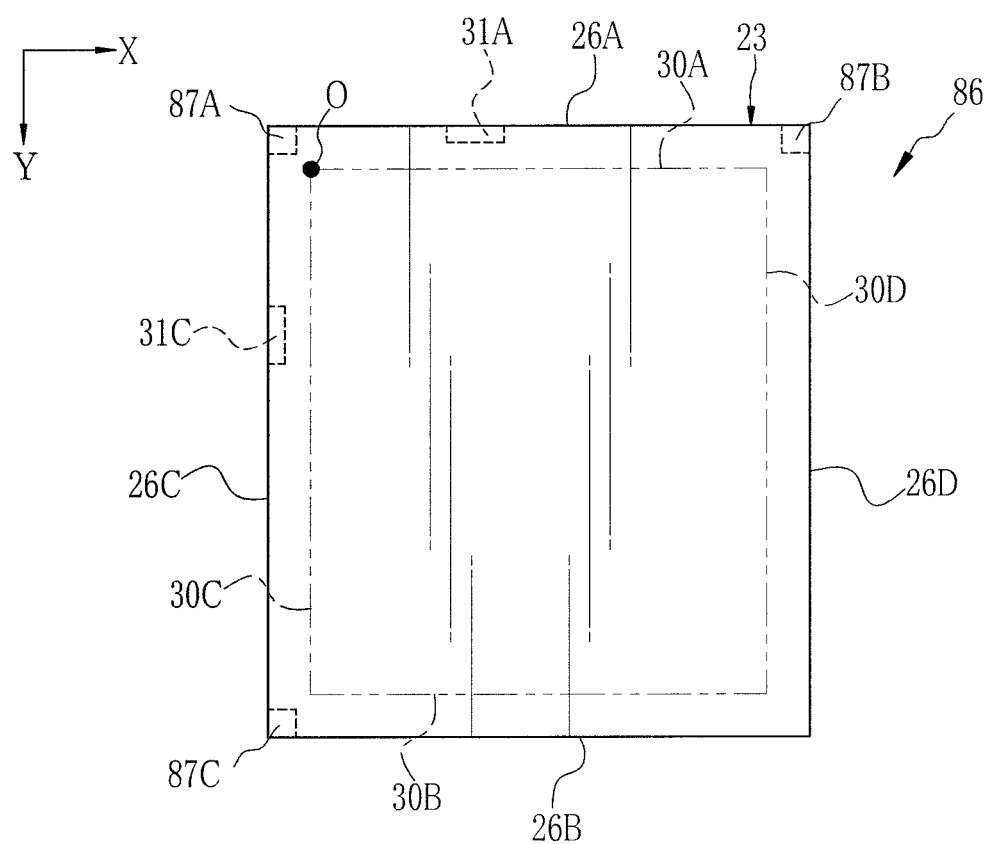
FIG. 26 is a schematic plan view of an external appearance of an electronic cassette of a fifth embodiment.
Figure 27:
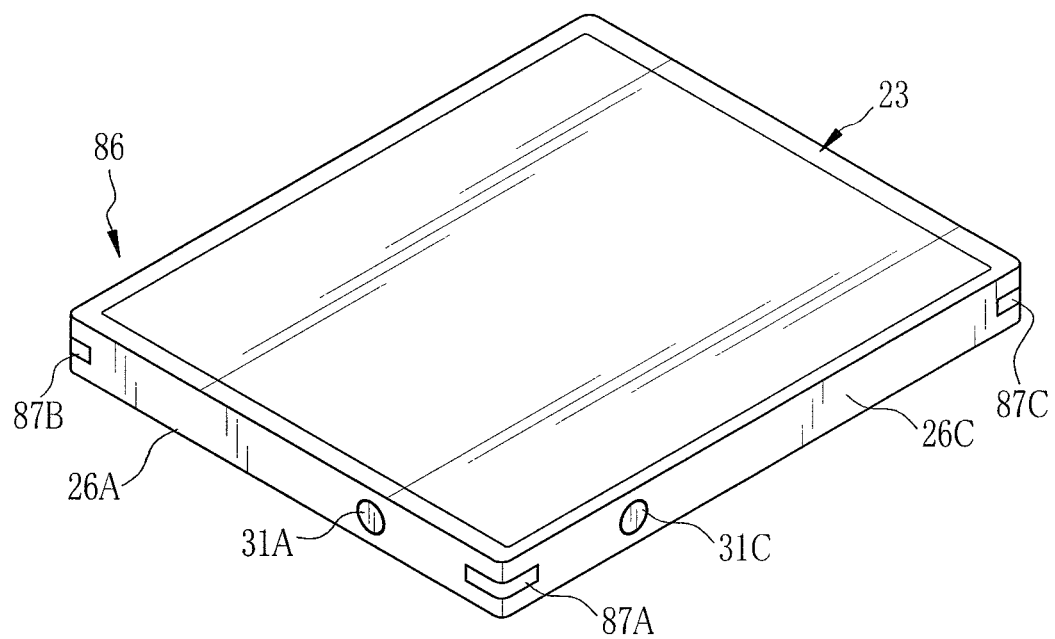
FIG. 27 is a diagrammatic perspective view of an external appearance of the electronic cassette of FIG. 26.

Moreover, it is possible to use only one operation button for selecting one of the four head-bottom setting conditions by making the four conditions distinguishable from different states of a lamp or lamps. For example, as shown in FIG. 25, using a lamp that can light selectively in three colors, e.g. red, green and blue, makes four conditions distinguishable, including the light-off state for one condition. Upon each pushdown of the operation button, the lamp states change cyclically. In the example shown in FIG. 25, the lamp is initially in the light-off state, and turned on in red upon the first pushdown operation. Upon the second pushdown operation, the lamp is turned green, and then turned blue upon the third pushdown operation. Upon the fourth pushdown operation, the lamp returns to the light-off state. The setting conditions for the head margin of the image change with the pushdown operations of the operation button, correspondingly to the four lamp states.

The fourth embodiment wherein any of the four sides of the imaging area can be set to be the head margin of the image is superior in operability to the embodiment wherein the head margin should be set on either of the two sides. Especially when the cable 63 is connected to the electronic cassette during the imaging, the fourth embodiment will exhibit a prominent effect. As set forth above with reference to FIG. 13, there may be a case where the drawing direction of the cable 63 is so limited by some circumferential conditions in a patients bedroom that the position of the electronic cassette 10 to the subject must be determined by the drawing direction of the cable 63. Even in that case, since it is possible to select the head-bottom direction of the electronic cassette from among the four directions, the positioning flexibility is improved.

Fifth Embodiment

In the fifth embodiment shown in FIGS. 26 to 30, lamps for indicating the head-bottom setting condition are disposed on side surfaces 26 at or across corners of a housing 23. In an electronic cassette 86 shown in FIGS. 26 and 27, first and second operation buttons 31A and 31C are disposed on a short side surface 26A and a long side surface 26C, respectively, such that either of two sides, a first short side 30A or a first long side 30C, can be set to be the head of the image, like the electronic cassette 10 in accordance with the first embodiment. Unlike the first embodiment, lamps 87A, 87B and 87C are respectively disposed at three corners of the housing 23. Other features of the electronic cassette 86 may be equal to those of the electronic cassette 10.

The lamp 87A is disposed at the corner at which the side surface 26A corresponding to the first short side 30A meets the side surface 26C corresponding to the first long side 30C. The lamp 87B is disposed at the corner at which the side surface 26A corresponding to the first short side 30A meets the side surface 26D corresponding to the second long side 30D. The lamp 87C is disposed at the corner at which the side surface 26C corresponding to the first long side 30C meets the side surface 26B corresponding to the second short side 30B. Since the lamps 87A to 87C are disposed at the corners between the short sides and the long sides of the housing 23, light from the individual lamps 87A to 87C is visible from two directions, i.e. from the long side and the short side.

When the first operation button 31A is turned on to set the head on the first short side 30A, the lamps 87A and 87B are turned on, whereas the lamp 87C is turned off. Meanwhile, when the second operation button 31C is turned on to set the head on the first long side 30C, the lamps 87A and 87C are turned on, whereas the lamp 87B is turned off. Thus, when either the first short side 30A or the first long side 30C is selected as the head margin of the image, two lamps on the opposite ends of the side surface 26A or 26C that corresponds to the selected side 30A or 30C are turned on.

When the electronic cassette 86 is inserted under the patient P, some of the corners of the housing 23 may become invisible. However, since two lamps on the opposite ends of the side surface 26A or 26C are turned on, if one of the three lamps is hindered, it is possible to see from the ON/OFF of other two lamps which side is set to be the head margin, the short side 30A or the long side 30C. Thus, providing three lamps 87A to 87C respectively on the three corners of the housing 23 makes it easier to confirm the head-bottom setting condition. The lamps 87A to 87C are mounted in a frame 28 (refer to FIG. 3) that is easy to process for mounting.

Figure 28:
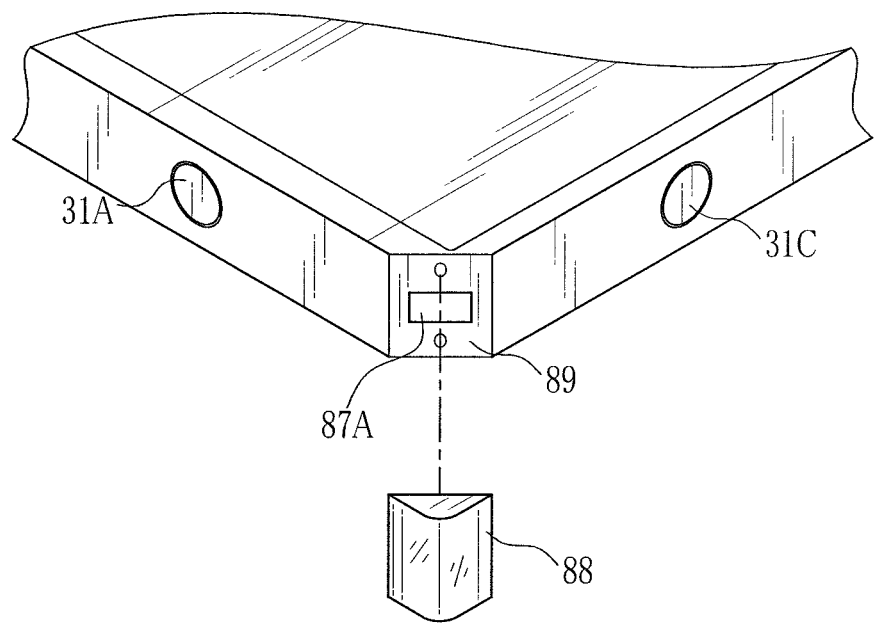
FIG. 28 is a perspective view of an aspect of a corner portion of the electronic cassette of FIG. 26.

As shown in FIG. 28, lamps 87A to 87C may be mounted each in a position inside a corner pad 88. The corner pad 88 is formed from an elastic material and attached to each corner of a housing 23 for the sake of impact protection of the electronic cassette. In the example shown in FIG. 28, the corner of the housing 23 is beveled to form a bevel face 89, and the lamp 87A is provided on the bevel face 89. Thereafter, the corner pad 88 is attached to the bevel face 89 to form a corner tip. The corner pad 88 is transparent to transmit light from the lamp 87A to the outside. Because the lamp 87A is covered with the corner pad 88, the lamp 87A is protected by the corner pad 88 from impacts. The lamps 87B and 87C are mounted in the same way as the lamp 87A.

Figure 29:
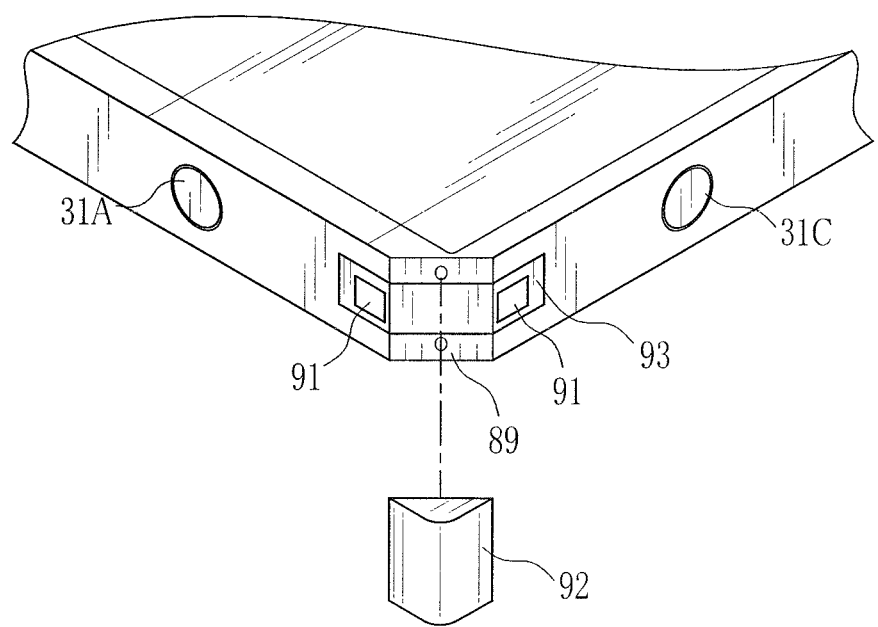
FIG. 29 is a perspective view of another aspect of a corner portion of the electronic cassette of FIG. 26.

It is also possible to provide two lamps 91 across a corner of a housing 23, as shown in FIG. 29. In this example, the corner of the housing 23 is diagonally cut to form a bevel face 89, and a corner pad 92 is attached as a corner tip of the housing 23 to the bevel face 89. The two lamps 91 are disposed on opposite sides of the corner pad 92, i.e. across the corner pad 92 that constitutes the corner of the housing 23. Disposing the lamps 91 this way makes light from either of the lamps 91 visible from two directions, i.e. from both the short side and the long side. As not covering the lamps 91, the corner pad 92 need not to be transparent. Furthermore, in this example, the lamps 91 are of a water-proof type provided on a flexible tape 93. Using a water-proof LED tape as the lamps 91 makes it easy to mount the lamps 91 because piercing the housing 23 is only necessary for wiring or the like.

Figure 30:
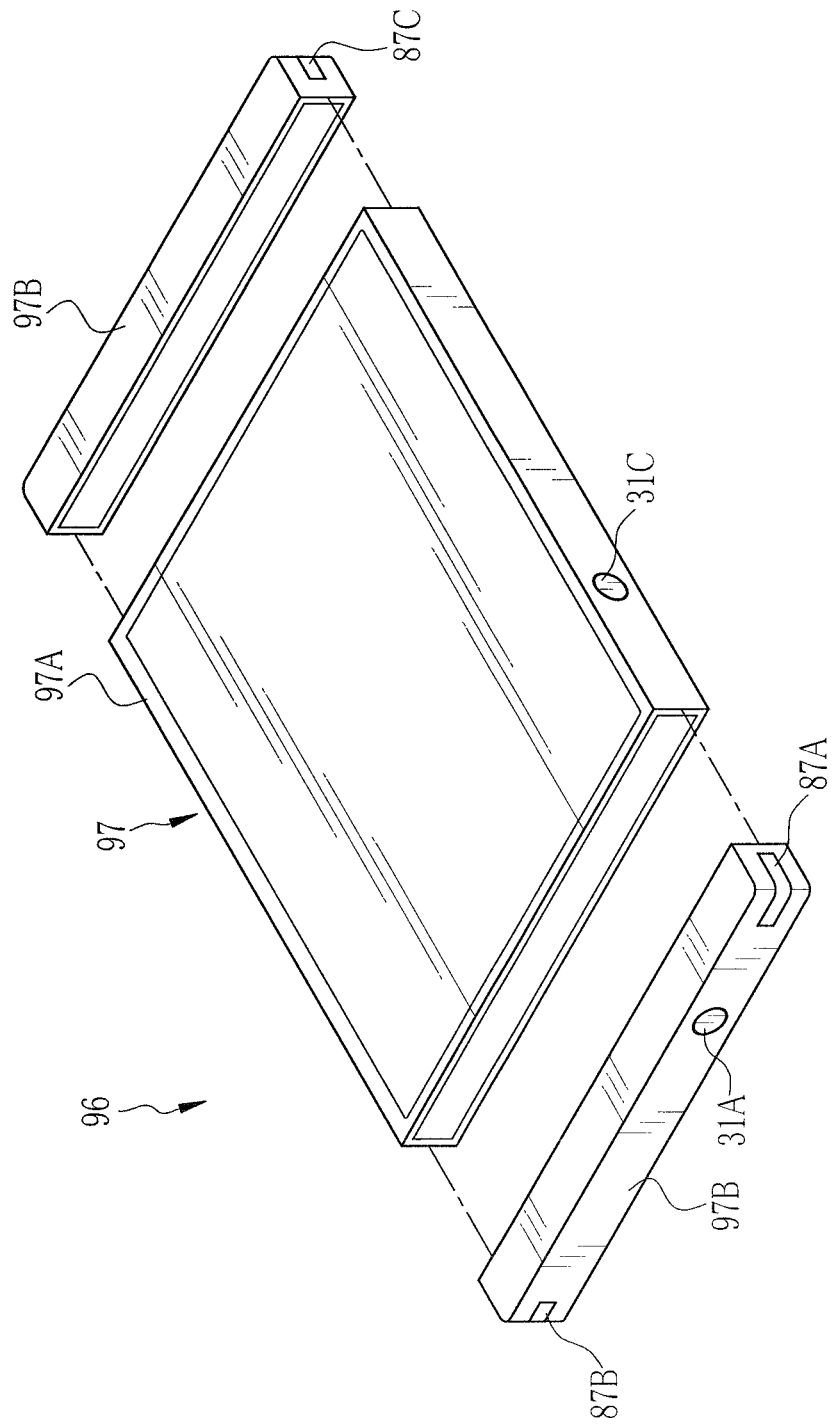
FIG. 30 is a perspective view of an electronic cassette having a housing of monocoque structure.

In an electronic cassette 96 which has a housing 97 of a monocoque structure, as shown in FIG. 30, lamps 87A to 87C may be disposed at corners of the housing 97. The monocoque structure housing 97 is constituted of a hollow main body 97A and a couple of end covers 97B that close opposite open ends of the main body 97A. The lamps 87A to 87C are provided at corners of the end covers 97B. According to this configuration of mounting the lamps 87A to 87C to the end covers 97B, treatment of the main body 97A for mounting the lamps 87A to 87C, such as piercing, becomes unnecessary or minimal. In an electronic cassette where the housing is of a monocoque structure and provided with corner pads, two lamps may be disposed across the corner pad that constitute a corner of the housing.

Figure 31:
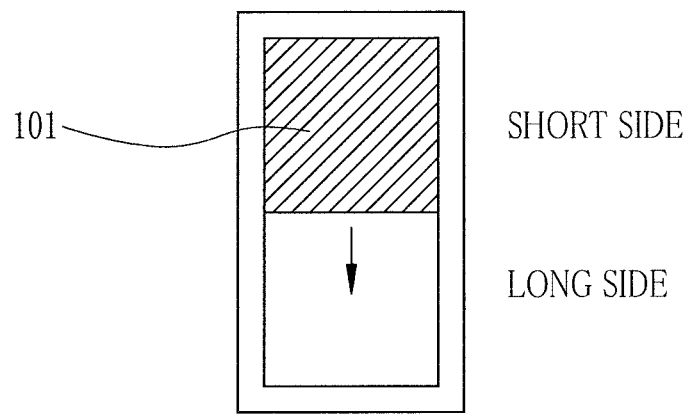
FIG. 31 is an explanatory diagram illustrating a slide switch.
Figure 32:
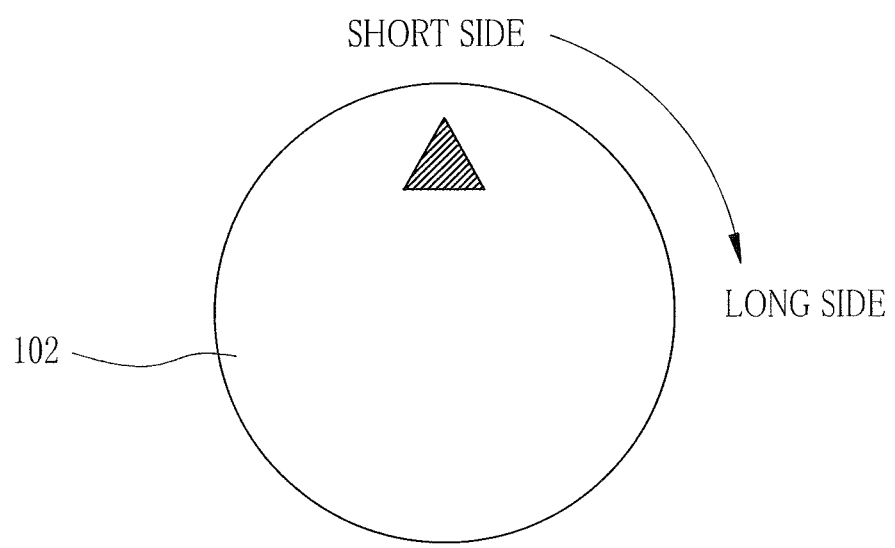
FIG. 32 is an explanatory diagram illustrating a dial switch.

In the above embodiments, the head-bottom setting is accomplished by selecting one side to be the head margin. Instead of that, it is possible to select one side to be the bottom margin. Although the above embodiments has been described while referring push buttons as an example of operating section, the operating section may be a slide switch 101 that is slid between two switching positions, as shown in FIG. 31, or a dial switch 102 that is turned between two switching positions, as shown in FIG. 32. In these cases, it is preferable to provide markers or signs representing "short side" and "long side" respectively at two switching positions of the slide switch 101 or the dial switch 102, so as to indicate which side is selected to be the head margin of the image.

It is also possible to utilize the head-bottom setting information for image processing, as shown in FIG. 33. An image processing table 103 defines that the image processing is changed between the vertically-long orientation where the short side is set to be the head margin and the horizontally-long orientation where the long side is set to be the head margin. As shown in FIGS. 9 and 10, an electronic cassette 10 may be used in the vertically-long orientation or the horizontally-long orientation depending on the trunk width of the individual patient P.

As shown in FIG. 10, to the patient P2 having a wider trunk width, the electronic cassette 10 is used in the horizontally-long orientation where the long side is set to be the head margin. Because the patient P2 having the wider trunk width tends to have a greater trunk thickness, the amount of X-rays penetrating therethrough is considered to decrease in comparison with the patient P1 with an average trunk width. An X-ray image 60 captured with the decreased amount of X-rays will have a relatively low density. Therefore, if the long side is set to be the head margin on the basis of the head-bottom setting information, an image processing device determines that the density of the image is insufficient and corrects the image to enhance the contrast as compared to standard image processing.

In order to change the contents of the image processing more properly, it is preferable to determine the necessity of the change by means of an index for the density of the X-ray image 60, such as an exposure index (EI), in addition to the head-bottom setting information.

As another example of serving the head-bottom setting information for other purpose than the automatic changing of the image display orientation, it is possible to change the threshold value for detecting the start of X-ray irradiation depending on the head-bottom direction of the electronic cassette during the imaging. For example, when the electronic cassette 10 is used in the horizontally-long orientation, it is considered that the patient as the subject has a wide trunk. In that case, the area in which the subject faces the imaging area 30 is relatively large, so the direct-incident area in which the X-rays are directly incident on the imaging area 30 without penetrating the subject will be reduced. As the direct-incident area decreases, it is assumed to take much time from the start of X-irradiation till the dose amount reaches the threshold value. Therefore, the threshold value may be lowered when the electronic cassette is used in the horizontally-long orientation, as for the vertically-long orientation.

Alternatively, the threshold value for detecting the start of X-ray irradiation may be set higher in the horizontally-long orientation where the long side is set to be the head margin, in comparison with the vertically-long orientation where the short side is set to be the head margin. For example, for the round-visit radiography or the like, the electronic cassette 10 may be used outside the imaging room under such circumstances that are at relatively high temperatures. If the temperature is high, dark currents in the imaging area could increase so much that the start of X-ray irradiation might be erroneously detected. In order to prevent the erroneous detection due to the dark current or other environmental noises under a high temperature circumstance, it is preferable to use the electronic cassette 10 in the horizontally-long orientation with the higher threshold value.

Although the present invention has been described with reference to those electronic cassettes which have an oblong rectangular imaging area 30, the present invention is applicable to such an electronic cassette that has a square imaging area. Furthermore, the electronic cassettes described above each have a rectangular top plan shape, but it is of course possible to apply the present invention to such an electronic cassette that is provided with a handling grip on one side of the housing.

It is apparent that the present invention is not limited to the above embodiments but various modifications are possible without departing from the subject matter of the present invention. For instance, the above various embodiments may be combined with each other, as appropriate. Moreover, the present invention is not limited to electronic cassettes using X-rays, but applicable to those using other radioactive rays such as gamma rays.

What is claimed is:

1. An electronic cassette comprising:
 a sensor panel that has a quadrangle imaging area and detects a radiographic image of a subject;
 a housing that houses the sensor panel;
 an operating section disposed on the housing;
 a head-bottom setting section that sets either one of at least adjoining two sides among four sides of the imaging area to be the head or the bottom of the radiographic image in the display orientation on the basis of an operation command from the operating section;
 a display section that is disposed on the housing and displays which side is set by the head-bottom setting section to be the head or the bottom of the radiographic image; and
 a memory for storing head-bottom setting information from the head-bottom setting section and the radiographic image in association with each other.

2. The electronic cassette of claim 1, wherein the memory stores a plurality of radiographic images in association with the individual head-bottom setting information.

3. The electronic cassette of claim 1, wherein the head-bottom setting section is capable of setting any one of the four sides to be the head or the bottom of the radiographic image.

4. The electronic cassette of claim 1, wherein the quadrangle imaging area is of an oblong rectangular shape wherein the adjoining two sides are a short side and a long side.

5. The electronic cassette of claim 1, further comprising a wireless communicator section for wirelessly transmitting the radiographic image stored in the memory, and a battery for supplying power to the sensor panel.

6. The electronic cassette of claim 1, further comprising a cable connector disposed on the housing, for connecting a cable for wired transmission of the radiographic image or power supply from an external power source.

7. The electronic cassette of claim 1, wherein the operating section can work with at least one of pushdown operation, sliding operation and turning operation.

8. The electronic cassette of claim 1, wherein the housing has a transparent panel which lets radioactive rays pass therethrough and a frame member for mounting the transparent panel therein, wherein at least one of the display section and the operating section is provided at the frame member.

9. The electronic cassette of claim 1, wherein the operating section is provided on at least one of four side surfaces of the housing, which correspond to the four sides of the imaging area.

10. The electronic cassette of claim 9, wherein the operating section is provided on at least two side surfaces of the housing, which correspond to the adjoining two sides of the imaging area.

11. The electronic cassette of claim 1, wherein the display section is provided on at least one of four side surfaces of the housing, which correspond to the four sides of the imaging area.

12. The electronic cassette of claim 11, wherein the display section is provided on at least two side surfaces of the housing, which correspond to the adjoining two sides.

13. The electronic cassette of claim 1, wherein the display section is provided at or across a corner at which adjoining two side surfaces of the housing meet.

14. The electronic cassette of claim 1, wherein the housing has four corners at each of which adjoining two side surfaces meet, and the display section is provided at or across each of three corners among the four corners.

15. The electronic cassette of claim 13, wherein a corner pad is provided at each corner of the housing, wherein the display section is disposed on either side of the corner pad or behind the corner pad.

16. The electronic cassette of claim 2, wherein the head-bottom setting section is capable of setting any one of the four sides to be the head or the bottom of the radiographic image.

17. The electronic cassette of claim 14, wherein a corner pad is provided at each corner of the housing, wherein the display section is disposed on either side of the corner pad or behind the corner pad.

* * * * *